United States Patent
Bootz et al.

(10) Patent No.: US 10,246,502 B2
(45) Date of Patent: Apr. 2, 2019

(54) IL22 IMMUNOCONJUGATES

(71) Applicant: PHILOGEN S.P.A., Siena (IT)

(72) Inventors: Franziska Sophie Bootz, Zürich (CH); Dario Neri, Buchs (CH)

(73) Assignee: Philogen S.P.A., Siena (IT)

( * ) Notice: Subject to any disclaimer, the term of this patent is extended or adjusted under 35 U.S.C. 154(b) by 0 days.

(21) Appl. No.: 15/608,689

(22) Filed: May 30, 2017

(65) Prior Publication Data
US 2017/0305989 A1 Oct. 26, 2017

Related U.S. Application Data

(63) Continuation of application No. PCT/EP2016/066979, filed on Jul. 15, 2016.

(30) Foreign Application Priority Data

Jul. 16, 2015 (GB) .................. 1512486.0
Oct. 6, 2015 (GB) .................. 1517649.8
Dec. 4, 2015 (GB) .................. 1521470.3

(51) Int. Cl.
| | | |
|---|---|---|
| C07K 14/54 | (2006.01) |
| C07K 16/18 | (2006.01) |
| C07K 19/00 | (2006.01) |
| A61K 38/20 | (2006.01) |
| A61K 47/68 | (2017.01) |
| C07K 16/30 | (2006.01) |
| C07K 14/78 | (2006.01) |
| A61K 38/00 | (2006.01) |
| A61K 39/00 | (2006.01) |

(52) U.S. Cl.
CPC .............. *C07K 14/54* (2013.01); *A61K 38/20* (2013.01); *A61K 47/6813* (2017.08); *A61K 47/6849* (2017.08); *A61K 47/6851* (2017.08); *C07K 16/18* (2013.01); *C07K 16/30* (2013.01); *C07K 19/00* (2013.01); *A61K 38/00* (2013.01); *A61K 2039/505* (2013.01); *C07K 2317/56* (2013.01); *C07K 2317/565* (2013.01); *C07K 2317/622* (2013.01); *C07K 2317/626* (2013.01); *C07K 2319/33* (2013.01); *C07K 2319/70* (2013.01)

(58) Field of Classification Search
None
See application file for complete search history.

(56) References Cited

U.S. PATENT DOCUMENTS

| 8,222,377 B2 | 7/2012 | Kaspar et al. |
| 8,481,684 B2 | 7/2013 | Rybak et al. |
| 2009/0068106 A1 | 3/2009 | Corti et al. |
| 2010/0183506 A1 | 7/2010 | Neri et al. |
| 2010/0260707 A1 | 10/2010 | Kaspar et al. |

FOREIGN PATENT DOCUMENTS

| WO | WO-2005/066348 A2 | 7/2005 |
| WO | WO-2006/119897 A2 | 11/2006 |
| WO | WO-2008/120101 A2 | 10/2008 |
| WO | WO-2009/056268 A1 | 5/2009 |
| WO | WO-2011/087986 A1 | 7/2011 |
| WO | WO-2014/145016 A2 | 9/2014 |
| WO | WO-2014/173570 A1 | 10/2014 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Bootz et al., "Alternatively spliced EDA domain of fibronectin is a target for pharmacodelivery applications in inflammatory bowel disease", Inflamm Bowel Dis. 21(8): 1908-17 (2015).
Bootz et al., "Antibody-based targeted delivery of interleukin-22 promotes rapid clinical recovery in mice with DSS-induced colitis", Inflamm Bowel Dis. 22(9):2098-105 (2016).
Bootz, Franziska, Slides from Doctoral Examination. "Antibody-Based Pharmacodelivery of Immunomodulators for the Treatment of Ulcerative Colitis," Swiss Federal Institute of Technology, Zurich (2015) (22 pages).
Bootz, Franziska, Thesis: "Antibody-Based Pharmacodelivery of Immunomodulators for the Treatment of Ulcerative Colitis," Doctor of Sciences, Swiss Federal Institute of Technology, Zurich (2016) (5 pages) (Abstract only).
Hemmerle et al., "Antibody-mediated delivery of interleukin 4 to the neo-vasculature reduces chronic skin inflammation", J Dermatol Sci. 76(2):96-103 (2014).
Hemmerle et al., "The antibody-based targeted delivery of interleukin-4 and 12 to the tumor neovasculature eradicates tumors in three mouse models of cancer", Int J Cancer. 134(2):467-77 (2013).
Hess et al., "The antibody-mediated targeted delivery of interleukin-13 to syngeneic murine tumors mediates a potent anticancer activity", Cancer Immunol Immunother. 64(5):635-44 (2015).
Hess et al., "Tumor-targeting properties of novel immunocytokines based on murine IL1beta and IL6", Protein Eng Des Sel. 27(6):207-13 (2014) (10 pages).

(Continued)

Primary Examiner — Bridget E Bunner
Assistant Examiner — Fozia Hamud
(74) Attorney, Agent, or Firm — Klarquist Sparkman, LLP

(57) ABSTRACT

The application relates to a conjugate comprising interleukin-22 (IL22) and an antibody molecule. The antibody molecule preferably binds an antigen associated with angiogenesis, such as the ED-A isoform of fibronectin. In particular, the application relates to the therapeutic use of such conjugates in the treatment of a disease/disorder, such as autoimmune diseases, including inflammatory bowel disease (IBD).

15 Claims, 10 Drawing Sheets

Specification includes a Sequence Listing.

(56) References Cited

OTHER PUBLICATIONS

Schwager et al., "Preclinical characterization of DEKAVIL (F8-IL10), a novel clinical-stage immunocytokine which inhibits the progression of collagen-induced arthritis", Arthritis Res Ther. 11(5):R142 (2009) (15 pages).
Smith et al., "IL-22 regulates iron availability in vivo through the induction of hepcidin". J. Immunol. 191(4):1845-55 (2013) (12 pages).
Sugimoto et al., "IL-22 ameliorates intestinal inflammation in a mouse model of ulcerative colitis", J Clin Invest. 118(2):534-44 (2008) (15 pages).
Brown et al., "Tolerance of single, but not multiple, amino acid replacements in antibody VH CDR 2: a means of minimizing B cell wastage from somatic hypermutation?" J Immunol. 156(9):3285-91 (1996).
Carnemolla et al., "Enhancement of the antitumor properties of interleukin-2 by its targeted delivery to the tumor blood vessel extracellular matrix," Blood. 99(5):1659-65 (2002).
Dickerson et al., "Enhancement of the antiangiogenic activity of interleukin-12 by peptide targeted delivery of the cytokine to alphavbeta3 integrin," Mol Cancer Res. 2(12):663-73 (2004).
Gafner et al., "An engineered antibody-interleukin-12 fusion protein with enhanced tumor vascular targeting properties," Int J Cancer. 119(9):2205-12 (2006).
Halin et al., "Enhancement of the antitumor activity of interleukin-12 by targeted delivery to neovasculature," Nat Biotechnol. 20(3):264-9 (2002).
International Preliminary Report on Patentability for International Patent Application No. PCT/EP2012/064490 dated Nov. 20, 2013 (12 pages).
International Search Report for International Patent Application No. PCT/EP2012/064490 dated Oct. 11, 2012 (5 pages).
Kontermann et al. *Antibody Engineering* vol. 2. 227-228 (2010).
Kontermann et al., "Intracellular and cell surface displayed single-chain diabodies" J Immunol Methods. 226(1-2):179-88 (1999) (Abstract Only).
Kriegsmann et al., "Expression of fibronectin splice variants and oncofetal glycosylated fibronectin in the synovial membranes of patients with rheumatoid arthritis and osteoarthritis," Rheumatol Int. 24(1):25-33 (2004).
Mårlind et al., "Antibody-mediated delivery of interleukin-2 to the stroma of breast cancer strongly enhances the potency of chemotherapy," Clin Cancer Res. 14(20):6515-24 (2008).
Nettelbeck et al., "Targeting of adenovirus to endothelial cells by a bispecific single-chain diabody directed against the adenovirus fiber knob domain and human endoglin (CD105)," Mol Ther. 3(6):882-91 (2001).
Pasche et al., "Cloning and characterization of novel tumor-targeting immunocytokines based on murine IL7," J Biotechnol. 154(1):84-92 (2011).
Pasche et al., "Immunocytokines: a novel class of potent armed antibodies," Drug Discov Today. 17(11-12):583-90 (2012).
Pasche et al., "The antibody-based delivery of interleukin-12 to the tumor neovasculature eradicates murine models of cancer in combination with paclitaxel," Clin Cancer Res. 18(15):4092-103 (2012).
Paul, Chapter 9: Structure and Function of Immunoglobulins. *Fundamental Immunology*, Third Edition. Raven Press Ltd., 292-295 (1993).
Rudikoff et al., "Single amino acid substitution altering antigen-binding specificity," Proc Natl Acad Sci U S A. 79(6):1979-83 (1982).
Sommavilla et al., "Expression, engineering and characterization of the tumor-targeting heterodimeric immunocytokine F8-IL12," Protein Eng Des Sel. 23(8):653-61 (2010).
Trachsel et al., "Antibody-mediated delivery of IL-10 inhibits the progression of established collagen-induced arthritis," Arthritis Res Ther. 9(1):R9 (2007) (9 pages).
Vajdos et al., "Comprehensive functional maps of the antigen-binding site of an anti-ErbB2 antibody obtained with shotgun scanning mutagenesis," J Mol Biol. 320(2):415-28 (2002).
Written Opinion of International Preliminary Examining Authority for International Patent Application No. PCT/EP2012/064490 dated Jul. 4, 2013 (6 pages).

* cited by examiner

"muIL22-F8"

"F8-muIL22"

"huIL22-F8"

IL22-F8

1. F8-IL22 reduced
2. F8-IL22 not reduced
3. F8-IL22 + PNGase reduced
4. F8-IL22 + PNGase not reduced

F8-IL22

1. IL22-F8 reduced
2. IL22-F8 not reduced
3. IL22-F8 + PNGase reduced
4. IL22-F8 + PNGase not reduced

IL22-F8

F8-IL22

IL22 IMMUNOCONJUGATES

FIELD OF THE INVENTION

The present invention relates to a conjugate comprising interleukin-22 (IL22) and an antibody molecule. The antibody molecule preferably binds an antigen associated with angiogenesis, such as the ED-A isoform of fibronectin. In particular, the present invention relates to the therapeutic use of such conjugates in the treatment of a disease/disorder, such as autoimmune diseases, including inflammatory bowel disease (IBD).

BACKGROUND TO THE INVENTION

Cytokines are key mediators of innate and adaptive immunity. Many cytokines have been used for therapeutic purposes in patients, such as those with advanced cancer, but their administration is typically associated with severe toxicity, hampering dose escalation to therapeutically active regimens and their development as anticancer drugs, for example. To overcome these problems, the use of Immunocytokines' (i.e. cytokines fused to antibodies or antibody fragments) has been proposed, with the aim to concentrate the immune-system stimulating activity at the site of disease while sparing normal tissues (Savage et al., 1993; Schrama et al., 2006; Neri et al. 2005; Dela Cruz et al., 2004; Reisfeld et al., 1997; Konterman et al., 2012).

For example, several pro-inflammatory immunocytokines (e.g., those based on IL2, IL12, IL15, TNF) have been shown to display a potent anti-tumoural effect in mouse models of cancer (Borsi et al. 2003; Carnemolla et al., 2002; Frey et al., 2010; Kaspar et al., 2007; Pasche et al., 2012). In contrast, anti-inflammatory immunocytokines (e.g., those based on IL10) have been shown to be capable of conferring a therapeutic benefit in mouse models of chronic inflammatory conditions (rheumatoid arthritis, endometriosis [Schwager et al. 2011; Schwager et al., 2009]) but have no impact on tumour growth.

Antibodies specific to splice-isoforms of fibronectin and of tenascin-C have been described as vehicles for pharmacodelivery applications, as these antigens are virtually undetectable in the normal healthy adult (with the exception of the placenta, endometrium and some vessels in the ovaries) while being strongly expressed in the majority of solid tumours and lymphomas (Brack et al., 2006; Pedretti et al, 2009; Schliemann et al. 2009). For example, antibodies F8 and L19, specific to the alternatively-spliced EDA and EDB domains of fibronectin, respectively, and anti-tenascin C antibody F16 (Brack et al., 2006; Villa et al., 2008; Viti et al., 1999), have been employed for the development of armed antibodies, some of which have begun clinical testing in oncology and in rheumatology (Eigentler et al., 2011; Papadia et al., 2012). The tumour targeting properties of these antibodies have also been documented in mouse models of cancer and in patients.

Interleukin 22 (IL22) is a 17 kDa globular cytokine belonging to the IL-10 family, which is mainly secreted by NK cells, dendritic cells and T-cells (Murphy 2012). It contains two intramolecular disulfide bonds and three N-linked glycosylation sites. Biological functions of IL22 include involvement in tissue protection, autoimmunity and inflammation. Secreted by lamina propria effector T-cells in the intestine, it induces mucin production, antimicrobial, proliferative and antiapoptotic pathways, which prevent tissue damage and promote epithelial repair. (Li et al., 2014). We investigated whether IL22 could be successfully fused to a vascular targeting antibody.

Cytokines can be conjugated to antibody molecules to produce immunocytokines as mentioned above. However, not all immunocytokines retain, for example, the in vivo targeting properties of the parental antibody (Pasche & Neri, 2012) or expected activities. The preparation of immunocytokines with therapeutic effects, such as anti-inflammatory activity, is therefore far from straightforward.

The preparation of conjugates comprising a mouse IgG1 Fc fused to the N-terminus or C-terminus of mouse IL-22 is described in Smith et al. (2013). These conjugates were prepared with a view to providing a more potent and longer-lasting IL-22R agonist compared with rIL-22. The purpose of the Fc region in this instance was therefore not to target IL22 to regions of disease, as was the case with the immunocytokines described in the preceding paragraph. In addition, Smith et al. (2013) shows that when the C-terminus of a murine Fc portion was fused to IL22 (Fc-IL-22), the fusion protein had higher activity than recombinant IL22, while when the N-terminus of a murine Fc portion was fused to IL22 (IL-22-Fc), the fusion protein had only minimal activity in vitro and no detectable activity in vivo.

STATEMENTS OF INVENTION

The present inventors have shown that IL22 can be conjugated to antibodies, which bind ED-A, while retaining not only the targeting properties of the unconjugated antibody but also the biological activity of IL22.

In one aspect, the present invention therefore relates to a conjugate comprising interleukin-22 (IL22) and an antibody molecule, or antigen-binding fragment thereof, which binds an antigen associated with angiogenesis. The present invention also relates to a nucleic acid molecule encoding such a conjugate, as well as an expression vector comprising such a nucleic acid. A host cell comprising such a vector is also encompassed by the present invention.

To the inventors' knowledge, the only document reporting the activity of IL-22 fused to an antibody portion is Smith et al. (2013). As mentioned above, Smith et al. (2013) shows that fusion of IL22 to the C-terminus of a murine Fc portion results in a fully active fusion protein, which has improved activity compared with recombinant IL22, while fusion of IL22 to the N-terminus of a murine Fc portion, results in a fusion protein which had minimal activity in vitro and no detectable activity in vivo. This data suggests that when preparing a fusion protein comprising IL22 and another polypeptide, such as an antibody portion, the N-terminus of IL22 should be fused to the C-terminus of said polypeptide in order for IL22 to retain its function.

However, the present inventors have surprisingly found that fusion of IL22 to the N-terminus of an antibody molecule, or antigen-binding fragment thereof, results in a conjugate with improved activity compared with a conjugate in which IL22 is fused to the C-terminus of the antibody molecule, or antigen-binding fragment thereof. Thus, in a preferred embodiment, the present invention relates to a conjugate comprising IL22 and an antibody molecule, or antigen-binding fragment thereof, which binds an antigen associated with angiogenesis, wherein IL22 is fused to the N-terminus of the antibody molecule, or antigen-binding fragment thereof.

The present invention also relates to a conjugate of the invention for use in a method for treatment of the human body by therapy. For example, the invention relates to a conjugate of the invention for use in a method of treating an autoimmune disease in a patient and to a conjugate of the invention for use in delivering IL22 to sites of autoimmune disease in a patient is also contemplated. A method of treating of an autoimmune disease in a patient, the method comprising administering a therapeutically effective amount of a conjugate of the invention to the patient also forms part of the inventions, as does a method of delivering IL22 to sites of autoimmune disease in a patient comprising administering the conjugate of the invention to the patient.

The present invention further relates to a conjugate of the invention for use in a method of treating an inflammation in a patient and to a conjugate of the invention for use in delivering IL22 to sites of inflammation in a patient is also contemplated. A method of treating inflammation in a patient, the method comprising administering a therapeutically effective amount of a conjugate of the invention to the patient also forms part of the invention, as does a method of delivering IL22 to sites of inflammation in a patient comprising administering the conjugate of the invention to the patient. The inflammation is preferably the result of an inflammatory disease and/or disorder.

DETAILED DESCRIPTION

Antibody Molecule

Figure 1A:
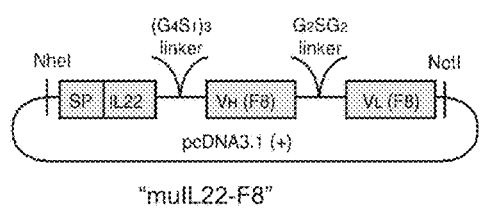
FIGS. 1A-1C are schematic diagrams of the mammalian cell expression vectors used to express the muIL22-F8 (FIG. 1A), F8-muIL22 (FIG. 1B), and huIL22-F8 conjugates (FIG. 1C).

This describes an immunoglobulin whether natural or partly or wholly synthetically produced.

The term also relates to any polypeptide or protein comprising an antibody antigen-binding site. It must be understood here that the antibody molecules may have been isolated or obtained by purification from natural sources, or else obtained by genetic recombination, or by chemical synthesis, and that they can contain unnatural amino acids.

As antibodies can be modified in a number of ways, the term "antibody molecule" should be construed as covering any specific binding member or substance having an antibody antigen-binding site with the required specificity and/or binding to antigen. Thus, this term covers antibody fragments, in particular antigen-binding fragments, and derivatives, including any polypeptide comprising an antibody antigen-binding site, whether natural or wholly or partially synthetic. Chimeric molecules comprising an antibody antigen-binding site, or equivalent, fused to another polypeptide (e.g. belonging to another antibody class or subclass) are therefore included. Cloning and expression of chimeric antibodies are described in EP-A-0120694 and EP-A-0125023, and a large body of subsequent literature.

As mentioned above, fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by an amino acid linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The half-life of antibody molecules for use in the present invention, or conjugates of the invention, may be increased by a chemical modification, especially by PEGylation, or by incorporation in a liposome.

An antibody molecule for use in the present invention preferably is, or comprises, an scFv. Diabodies, for example, comprise two scFv molecules. Most preferably, the antibody molecule for use in the present invention is a diabody. Diabodies and scFvs do not comprise an antibody Fc region, thus potentially reducing the effects of anti-idiotypic reactions.

Where the antibody molecule is a diabody, the VH and VL domains are preferably linked by a 5 to 12 amino acid linker. A diabody comprises two VH-VL molecules which associate to form a dimer. The VH and VL domains of each VH-VL molecule are preferably linked by a 5 to 12 amino acid linker. For example, the VH and VL domains may be linked by an amino acid linker which is 5, 6, 7, 8, 9, 10, 11, or 12 amino acid in length. Preferably, the amino acid linker is 5 amino acids in length. Suitable linker sequences are known in the art and include the linker sequence set forth in SEQ ID NO: 9.

Where the antibody molecule is an scFv, the VH and VL domains of the antibody are preferably linked by a 14 to 20 amino acid linker. For example, the VH and VL domains may be linked by an amino acid linker which is 14, 15, 16, 17, 18, 19, or 20 amino acid in length. Suitable linker sequences are known in the art and include the linker sequence set forth in SEQ ID NO: 43.

The present inventors have shown that a conjugate comprising IL22 and an antibody molecule which binds the Extra-Domain A (ED-A) of fibronectin can successfully, and specifically, target tumour tissue in vivo. The ED-A isoform of fibronectin is known to be expressed in neovasculature, such as the neovasculature found in tumours, but not in healthy tissues. This data therefore provides evidence that a conjugate comprising IL22 and an antibody molecule which binds the ED-A of fibronectin can be used to target sites of angiogenesis. IL22 conjugates therefore are suitable for treating inflammation and autoimmune diseases in an individual. Many autoimmune diseases, as well as diseases associated with inflammation, are known to involve and/or be characterised by angiogenesis.

It is expected that other conjugates comprising IL22 and an antibody molecule which binds an antigen associated with angiogenesis will similarly be suitable to target IL22 to sites of angiogenesis and thus find application in the treatment of autoimmune diseases and/or inflammation. Many such antigens are known in the art, as are antibodies capable of binding such antigens. In additions, antibodies against a given antigen can be generated using well-known methods such as those described in the present application. In one example, the antigen may be an extra-cellular matrix component associated with angiogenesis, such as a fibronectin, including the Extra-Domain A (ED-A) isoform of fibronectin (A-FN), the Extra-Domain B (ED-B) isoform of fibronectin (B-FN), tenascin C, the ED-A of fibronectin, the ED-B of fibronectin, or the A1 Domain of Tenascin C. Antibodies which bind the ED-A of fibronectin, and thus also A-FN, are known in the art and include antibody F8. Antibodies which bind the ED-B of fibronectin, or the A1 Domain of Tenascin C (and thus also the B-FN and tenascin C) are also known in the art and include antibodies L19 and F16, respectively. Antibodies which bind the ED-B of fibronectin, or the A1 Domain of Tenascin C, including antibodies L19 and F16, have been shown to be capable of specifically targeting neovasculature in vivo. It is thus expected that conjugates comprising IL22 and an antibody molecule which binds B-FN, tenascin C, the ED-B of fibronectin, or the A1 Domain of Tenascin C, will be capable of targeting IL22 to neovasculature, in the same way as a conjugate comprising IL22 and an antibody molecule which binds A-FN, as demonstrated using antibody F8 herein and thus find application in the treatment of autoimmune diseases and/or inflammation.

Thus an antibody molecule for use in the invention binds an antigen associated with angiogenesis. Preferably, antibody molecule for use in the invention binds an extra-cellular matrix component associated with angiogenesis, such as A-FN, B-FN, tenascin C, the ED-A of fibronectin, the ED-B of fibronectin, or the A1 Domain of Tenascin C. More preferably, an antibody molecule for use in the invention binds the A-FN or the ED-A of fibronectin. Most preferably, an antibody molecule for use in the invention binds the ED-A of fibronectin.

In a preferred embodiment, an antibody molecule for use in the invention may have the CDRs and/or the VH and/or VL domains of antibodies F8, L19 or F16 described herein. An antibody molecule for use in the invention preferably has the CDRs of antibody F8 set forth in SEQ ID NOs 1-6. More preferably, an antibody for use in the invention comprises the VH and/or VL domains of antibody F8 set forth in SEQ ID NOs 7 and 8. Yet more preferably, an antibody for use in the invention comprises the VH and VL domains of antibody F8 set forth in SEQ ID NOs 7 and 8. The F8 antibody is preferably in diabody or scFv format, most preferably in diabody format. Where the F8 antibody is in diabody format, the antibody molecule for use in the invention preferably has the amino acid sequence set forth in SEQ ID NO: 10.

An antibody molecule for use in the invention may bind the A-FN and/or the ED-A of fibronectin, with the same affinity as anti-ED-A antibody F8 e.g. in diabody format, or with an affinity that is better. An antibody molecule for use in the invention may bind the B-FN and/or the ED-B of fibronectin, with the same affinity as anti-ED-B antibody L19 e.g. in diabody format, or with an affinity that is better. An antibody molecule for use in the invention may bind the Tenascin C and/or the A1 domain of tenascin C, with the same affinity as anti-ED-A antibody F16 e.g. in diabody format, or with an affinity that is better.

An antibody molecule for use in the invention may bind to the same epitope on A-FN and/or the ED-A of fibronectin as anti-ED-A antibody F8. An antibody molecule for use in the invention may bind to the same epitope on B-FN and/or the ED-B of fibronectin as anti-ED-A antibody L19. An antibody molecule for use in the present invention may bind to the same epitope on tenascin C and/or the A1 domain of tenascin C as antibody F16.

Variants of antibody molecules disclosed herein may be produced and used in the present invention. The techniques required to make substitutions within amino acid sequences of CDRs, antibody VH or VL domains, in particular the framework regions of the VH and VL domains, and antibody molecules generally are available in the art. Variant sequences may be made, with substitutions that may or may not be predicted to have a minimal or beneficial effect on activity, and tested for ability to bind A-FN and/or the ED-A of fibronectin, B-FN and/or the ED-B of fibronectin, tenascin C and/or the A1 domain of tenascin C, and/or for any other desired property.

It is contemplated that from 1 to 5, e.g. from 1 to 4, including 1 to 3, or 1 or 2, or 3 or 4, amino acid alterations (addition, deletion, substitution and/or insertion of an amino acid residue) may be made in one or more of the CDRs and/or the VH and/or the VL domain of an antibody molecule as described herein. Thus, an antibody molecule which binds the FN-A, FN-B, or tenascin C, may comprise the CDRs and/or the VH and/or the VL domain of antibody F8, L19, or F16 described herein with 5 or fewer, for example, 5, 4, 3, 2 or 1 amino acid alterations within the CDRs and/or the VH and/or the VL domain. For example, an antibody molecule which binds the FN-A, FN-B, or tenascin C, may comprise the VH and/or the VL domain of antibody F8, L19, or F16 described herein with 5 or fewer, for example, 5, 4, 3, 2 or 1 amino acid alterations within the framework region of the VH and/or VL domain. An antibody molecule that binds the FN-A or ED-A of fibronectin, as referred to herein, thus may comprise the VH domain shown in SEQ ID NO: 7 and/or the VL domain set forth in SEQ ID NO: 8 with 5 or fewer, for example, 5, 4, 3, 2 or 1 amino acid alterations within the framework region of the VH and/or VL domain. Such an antibody molecule may bind the ED-A isoform or ED-A of fibronectin with the same or substantially the same, affinity as an antibody molecule comprising the VH domain set forth in SEQ ID NO: 7 and the VL domain shown in SEQ ID NO: 8 or may bind the ED-A isoform or ED-A of fibronectin with a higher affinity than an antibody molecule comprising the VH domain set forth in SEQ ID NO: 7 and the VL domain set forth in SEQ ID NO: 8.

An antibody molecule for use in the invention may comprise a VH and/or VL domain that has at least 70%, more preferably one of at least 75%, 80%, 85%, 90%, 95%, 96%, 97%, 98%, 99% or 100%, sequence identity to the VH and/or VL domain, as applicable, of antibody F8, L19, or F16 set forth in SEQ ID NOs 7, 8, 31, 32, 40, and 41. An antibody molecule for use in the invention may have at least 70%, more preferably one of at least 75%, 80%, 85%, 90%, 95%, 96%, 97%, 98%, 99% or 100%, sequence identity to the amino acid sequence of the F8, L19, or F16 antibodies set forth in SEQ ID NOs 10, 33, and 42, respectively.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Antigen-Binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site preferably comprises an antibody light chain variable region (VL) and an antibody heavy chain variable region (VH).

An antigen binding site may be provided by means of arrangement of complementarity determining regions (CDRs). The structure for carrying a CDR or a set of CDRs will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. (1987) (Sequences of Proteins of Immunological Interest. 4$^{th}$ Edition. US Department of Health and Human Services.), and updates thereof, now available on the Internet (at immuno.bme.nwu.edu or find "Kabat" using any search engine).

By CDR region or CDR, it is intended to indicate the hypervariable regions of the heavy and light chains of the immunoglobulin as defined by Kabat et al. (1987) Sequences of Proteins of Immunological Interest, 4$^{th}$ Edition, US Department of Health and Human Services (Kabat et al., (1991a), Sequences of Proteins of Immunological Interest, 5$^{th}$ Edition, US Department of Health and Human Services, Public Service, NIH, Washington, and later editions). An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It can be as short as 2 amino acids although the longest size known is 26. Functionally, HCDR3 plays a role in part in the determination of the specificity of the antibody (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144: 4863-4869; Kabat et al., (1991b), J. Immunol., 147:1709-1719).

An antigen binding site forming part of an antibody molecule for use in the invention preferably has the CDRs of antibody F8 set forth in SEQ ID NOs 1-6, the CDRs of antibody L19 set forth in SEQ ID NOs 25-30, or the CDRs of antibody F16 set forth in SEQ ID NOs 34-39. Most preferably, an antigen binding site forming part of an antibody molecule for use in the invention has the CDRs of antibody F8 set forth in SEQ ID NOs 1-6.

Preparation and Selection of Antibody Molecules

Various methods are available in the art for obtaining antibodies molecules against a target antigen. The antibody molecules for use in the present invention are preferably monoclonal antibodies, especially of human, murine, chimeric or humanized origin, which can be obtained according to the standard methods well known to the person skilled in the art. An antibody molecule for use in the present invention is most preferably a human antibody molecule.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody molecule to the constant regions, or constant regions plus framework regions, of a different immunoglobulin. See, for instance, EP-A-184187, GB 2188638A or EP-A-239400, and a large body of subsequent literature. A hybridoma or other cell producing an antibody may also be subject to genetic mutation or other changes, which may or may not alter the binding specificity of antibodies produced.

Techniques available in the art of antibody engineering have made it possible to isolate human and humanised antibodies. For example, human hybridomas can be made as described by Kontermann & Dubel (2001), S, *Antibody Engineering*, Springer-Verlag New York, LLC; ISBN: 3540413545. Phage display, another established technique for generating specific binding members has been described in detail in many publications such as WO92/01047 (discussed further below) and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160, U.S. Pat. No. 6,521,404 and Kontermann & Dubel (2001), S, *Antibody Engineering*, Springer-Verlag New York, LLC; ISBN: 3540413545. Transgenic mice in which the mouse antibody genes are inactivated and functionally replaced with human antibody genes while leaving intact other components of the mouse immune system, can be used for isolating human antibodies (Mendez et al., (1997), Nature Genet, 15(2): 146-156).

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein, 1975, Nature, 256:495-497.

Monoclonal antibodies can be obtained, for example, from an animal cell immunized against the an antigen associated with angiogenesis, such as A-FN, B-FN, tenascin C, the ED-A of fibronectin, the ED-B of fibronectin, or the A1 Domain of Tenascin C, according to the usual working methods, by genetic recombination starting with a nucleic acid sequence contained in the cDNA sequence coding for A-FN, B-FN, or tenascin C, or fragment thereof, or by peptide synthesis starting from a sequence of amino acids comprised in the peptide sequence of the A-FN, B-FN, or tenascin C, and/or a fragment thereof.

Synthetic antibody molecules may be created by expression from genes generated by means of oligonucleotides synthesized and assembled within suitable expression vectors, for example as described by Knappik et al. (2000) J. Mol. Biol. 296, 57-86 or Krebs et al. (2001) Journal of Immunological Methods, 254 67-84.

Alternatively, one or more antibody molecules for an antigen associated with angiogenesis, such as the A-FN, the ED-A, B-FN, the ED-B, tenascin C, or the A1 domain of tenascin C may be obtained by bringing into contact a library of antibody molecules and the antigen or a fragment thereof, e.g. a fragment comprising or consisting of ED-A, ED-B, or the A1 domain of tenascin C, or a peptide fragment thereof, and selecting one or more antibody molecules of the library able to bind the antigen.

An antibody library may be screened using Iterative Colony Filter Screening (ICFS). In ICFS, bacteria containing the DNA encoding several binding specificities are grown in a liquid medium and, once the stage of exponential growth has been reached, some billions of them are distributed onto a growth support consisting of a suitably pre-treated membrane filter which is incubated until completely confluent bacterial colonies appear. A second trap substrate consists of another membrane filter, pre-humidified and covered with the desired antigen.

The trap membrane filter is then placed onto a plate containing a suitable culture medium and covered with the growth filter with the surface covered with bacterial colonies pointing upwards. The sandwich thus obtained is incubated at room temperature for about 16 h. It is thus possible to obtain the expression of the genes encoding antibody fragments scFv having a spreading action, so that those fragments binding specifically with the antigen which is present on the trap membrane are trapped. The trap membrane is then treated to point out bound antibody fragments scFv with colorimetric techniques commonly used to this purpose.

The position of the coloured spots on the trap filter allows one to go back to the corresponding bacterial colonies which are present on the growth membrane and produced the antibody fragments trapped. Such colonies are gathered and grown and the bacteria-a few millions of them are distributed onto a new culture membrane repeating the procedures described above. Analogous cycles are then carried out until the positive signals on the trap membrane correspond to single positive colonies, each of which represents a potential source of monoclonal antibody fragments directed against the antigen used in the selection. ICFS is described in e.g. WO0246455.

A library may also be displayed on particles or molecular complexes, e.g. replicable genetic packages such bacteriophage (e.g. T7) particles, or other in vitro display systems, each particle or molecular complex containing nucleic acid encoding the antibody VH variable domain displayed on it, and optionally also a displayed VL domain if present. Phage display is described in WO92/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404.

Following selection of antibody molecules able to bind the antigen and displayed on bacteriophage or other library particles or molecular complexes, nucleic acid may be taken from a bacteriophage or other particle or molecular complex displaying a said selected antibody molecule. Such nucleic acid may be used in subsequent production of an antibody molecule or an antibody VH or VL variable domain by expression from nucleic acid with the sequence of nucleic acid taken from a bacteriophage or other particle or molecular complex displaying a said selected antibody molecule.

Ability to bind an antigen associated with angiogenesis, such as the A-FN, B-FN, the ED-A, or the ED-B of fibronectin, tenascin C or the A1 domain of tenascin C or other target antigen or isoform may be further tested, e.g. ability to compete with an antibody specific for the A-FN, B-FN, the ED-A, or the ED-B of fibronectin, tenascin C or the A1 domain of tenascin C, such as antibody F8, L19, or F16.

Novel VH or VL regions carrying CDR-derived sequences for use in the invention may be also generated using random mutagenesis of one or more selected VH and/or VL genes to generate mutations within the entire variable domain. In some embodiments one or two amino acid substitutions are made within an entire variable domain or set of CDRs. Another method that may be used is to direct mutagenesis to CDR regions of VH or VL genes.

Variable domains employed in the invention may be obtained or derived from any germ-line or rearranged human variable domain, or may be a synthetic variable domain based on consensus or actual sequences of known human variable domains. A variable domain can be derived from a non-human antibody. A CDR sequence for use in the invention (e.g. CDR3) may be introduced into a repertoire of variable domains lacking a CDR (e.g. CDR3), using recombinant DNA technology. For example, Marks et al. (1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide antibody molecules for use in the invention. The repertoire may then be displayed in a suitable host system such as the phage display system of WO92/01047, or any of a subsequent large body of literature, including Kay, Winter & McCafferty (1996), so that suitable antibody molecules may be selected. A repertoire may consist of from anything from $10^4$ individual members upwards, for example at least $10^5$, at least $10^6$, at least $10^7$, at least $10^8$, at least $10^9$ or at least $10^{10}$ members.

An antigen associated with angiogenesis, such as the A-FN, B-FN, the ED-A, or the ED-B of fibronectin, tenascin C or the A1 domain of tenascin C may be used in a screen for antibody molecules, e.g. antibody molecules, for use in the invention. The screen may a screen of a repertoire as disclosed elsewhere herein.

Similarly, one or more, or all three CDRs may be grafted into a repertoire of VH or VL domains that are then screened for an antibody molecule or antibody molecules for an antigen associated with angiogenesis, such as A-FN, B-FN, the ED-A, or the ED-B of fibronectin, tenascin C or the A1 domain of tenascin C. One or more of the HCDR1, HCDR2 and HCDR3 of antibody F8, L19, or F16, or the set of HCDRs of antibody F8, L19, or F16 may be employed, and/or one or more of the LCDR1, LCDR2 and LCDR3 of antibody F8, L19, or F16 the set of LCDRs of antibody F8, L19, or F16 may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibody molecules of the present invention made by recombinant DNA techniques may result in the introduction of N- or C-terminal residues encoded by linkers introduced to facilitate cloning or other manipulation steps. Other manipulation steps include the introduction of linkers to join variable domains disclosed elsewhere herein to further protein sequences including antibody constant regions, other variable domains (for example in the production of diabodies) or detectable/functional labels as discussed in more detail elsewhere herein.

Although antibody molecules may comprise a pair of VH and VL domains, single binding domains based on either VH or VL domain sequences may also be used in the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain antibody molecule able to bind an antigen associated with angiogenesis, such as A-FN, B-FN, the ED-A, or the ED-B of fibronectin, tenascin C or the A1 domain of tenascin C. This may be achieved by phage display screening methods using the so-called hierarchical dual combinatorial approach as disclosed in WO92/01047, in which an individual colony containing either an H or L chain clone is used to infect a complete library of clones encoding the other chain (L or H) and the resulting two-chain antibody molecule is selected in accordance with phage display techniques such as those described in that reference. This technique is also disclosed in Marks 1992.

Fragments of whole antibodies for use in the invention can be obtained starting from any of the antibody molecules described herein, e.g. antibody molecules comprising VH and/or VL domains or CDRs of any of antibodies described herein, by methods such as digestion by enzymes, such as pepsin or papain and/or by cleavage of the disulfide bridges by chemical reduction. In another manner, antibody fragments may be obtained by techniques of genetic recombination likewise well known to the person skilled in the art or else by peptide synthesis by means of, for example, automatic peptide synthesizers such as those supplied by the company Applied Biosystems, etc., or by nucleic acid synthesis and expression.

Conjugate

A conjugate according to the present invention comprises IL22 and an antibody molecule which binds an antigen associated with angiogenesis, as described herein. The antibody molecule is preferably a diabody or an scFv, most preferably a diabody, as described herein.

The IL22 is preferably human IL22. Typically, IL22 has at least 70%, more preferably one of at least 75%, 80%, 85%, 90%, 95%, 96%, 97%, 98%, 99% or 100%, sequence identity to the amino acid sequence set forth in SEQ ID NO: 11. IL22 in conjugates of the invention retains a biological activity of human IL22, e.g. the ability to inhibit inflammation. Most preferably, the IL22 comprises or consist of the sequence set forth in SEQ ID NO: 11.

The inventors expect that IL22 is glycosylated at the asparagine residues at positions 21, 35 and 64 in SEQ ID NO:11. Two glycosylation sites have been described for insect cell based production (Acta Crystallogr D Biol Crystallogr. 2005 July; 61(Pt 7):942-50. Epub 2005 Jun. 24.) The third one was obtained using sequence analysis. The inventors also predict that substitution of the asparagine residues at positions 21, 35 and 64 with glutamine will prevent glycosylation of IL22 at these residues. It is generally preferable to avoid glycosylation, as glycosylation may interfere with conjugate production, including batch consistency, and result in more rapid clearance of the conjugate from the patient's body. Preferably, a conjugates of the present invention, and in particular the IL22 present in a conjugate of the present invention, is not glycosylated. Thus, IL22 may comprise or consist of the sequence shown in SEQ ID NO: 11, except that the residue at position 21, and/or position 35, and/or position 64 of SEQ ID NO: 11 is a glutamine residue rather than an asparagine residue.

Preferably, the antibody molecule is connected to the IL22 through a linker, preferably an amino acid linker. Alternatively, the antibody molecule and IL22 may be connected directly, e.g. through a chemical bond.

Where the antibody molecule is a two-chain or multi-chain molecule, IL22 may be connected to one or more polypeptide chains in the antibody molecule by means of an amino acid linker, or connected directly to one or more polypeptide chains in the antibody molecule.

The chemical bond may be, for example, a covalent or ionic bond. Examples of covalent bonds include peptide bonds (amide bonds) and disulphide bonds. The antibody molecule and IL22 may be covalently linked, for example by peptide bonds (amide bonds).

Where the antibody molecule is linked to IL22 by means of an amino acid linker, the conjugate may be or comprise a fusion protein. By "fusion protein" is meant a polypeptide that is a translation product resulting from the fusion of two or more genes or nucleic acid coding sequences into one open reading frame (ORF). Where the conjugate comprises a diabody, the two scFv molecules making up the diabody (each of which is preferably linked to IL22 via and amino acid linker) may each be expressed as a fusion protein and then allowed to associate to form a dimer.

The amino acid linker connecting the antibody molecule and IL22 may be a flexible amino acid linker. Suitable examples of amino acid linker sequences are known in the art. The linker may be 10-20 amino acids, preferably 10-15 amino acids in length. Most preferably, the linker is 11-15 amino acids in length. The linker may have the sequence set forth in SEQ ID NO: 12.

IL22 may be connected, either through an amino acid linker, or directly, to the N-terminus or C-terminus of the antibody molecule. Preferably, IL22 is connected to the N-terminus of the antibody molecule.

IL22 may be connected, either through an amino acid linker, or directly, via its C-terminus or N-terminus to the antibody molecule. Preferably, IL22 is connected via its C-terminus to the antibody molecule.

In the conjugate employed in the present examples, IL22 from mus musculus (muIL22) was conjugated via an amino acid linker to either the VH domains or the VL domains of two scFv molecules making up a diabody, as shown in SEQ ID NOs 23 and 24. Both conjugates were shown to be capable of specifically targeting neovasculature. Thus, where the antibody molecule is, or comprises, an scFv, IL22 may be linked to the N-terminus of the VH domain of the scFv via an amino acid linker or to the C-terminus of the VL domain of the scFv via an amino acid linker. Preferably, IL22 is connected to the N-terminus of the VH domain of the scFv, most preferably via an amino acid linker.

The conjugate of the present invention may comprise or consist of the sequence shown in SEQ ID NO: 16 or 17. The conjugate may have at least 70%, more preferably one of at least 75%, 80%, 85%, 90%, 95%, 96%, 97%, 98%, 99% or 100%, sequence identity to the amino acid sequence shown in SEQ ID NO: 16 or 17.

The conjugate of the present invention may be deglycosylated. Methods for deglycosylating a polypeptide are known in the art and include treatment with Peptide-N-Glycosidase F (PNGase F).

Nucleic Acids

Also provided is an isolated nucleic acid molecule encoding a conjugate according to the present invention. Nucleic acid molecules may comprise DNA and/or RNA and may be partially or wholly synthetic. Reference to a nucleotide sequence as set out herein encompasses a DNA molecule with the specified sequence, and encompasses a RNA molecule with the specified sequence in which U is substituted for T, unless context requires otherwise.

Further provided are constructs in the form of plasmids, vectors (e.g. expression vectors), transcription or expression cassettes which comprise such nucleic acids. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate. For further details see, for example, Sambrook & Russell (2001) Molecular Cloning: a Laboratory Manual: 3rd edition, Cold Spring Harbor Laboratory Press. Many known techniques and protocols for manipulation of nucleic acid, for example in the preparation of nucleic acid constructs, mutagenesis, sequencing, introduction of DNA into cells and gene expression, and analysis of proteins, are described in detail in Ausubel et al. (1999) 4$^{th}$ eds., Short Protocols in Molecular Biology: A Compendium of Methods from Current Protocols in Molecular Biology, John Wiley & Sons.

Host Cells

A recombinant host cell that comprises one or more constructs as described above is also provided. Suitable host cells include bacteria, mammalian cells, plant cells, filamentous fungi, yeast and baculovirus systems and transgenic plants and animals.

A conjugate according to the present invention may be produced using such a recombinant host cell. The production method may comprise expressing a nucleic acid or construct as described above. Expression may conveniently be achieved by culturing the recombinant host cell under appropriate conditions for production of the conjugate. Following production the conjugate may be isolated and/or purified using any suitable technique, and then used as appropriate. The conjugate may be formulated into a composition including at least one additional component, such as a pharmaceutically acceptable excipient.

Systems for cloning and expression of a polypeptide in a variety of different host cells are well known. The expression of antibodies, including conjugates thereof, in prokaryotic cells is well established in the art. For a review, see for example Plückthun (1991), Bio/Technology 9: 545-551. A common bacterial host is E. coli.

Expression in eukaryotic cells in culture is also available to those skilled in the art as an option for production of conjugates for example Chadd et al. (2001), Current Opinion in Biotechnology 12: 188-194); Andersen et al. (2002) Current Opinion in Biotechnology 13: 117; Larrick & Thomas (2001) Current Opinion in Biotechnology 12:411-418. Mammalian cell lines available in the art for expression of a heterologous polypeptide include Chinese hamster ovary (CHO) cells, HeLa cells, baby hamster kidney cells, NSO mouse melanoma cells, YB2/0 rat myeloma cells, human embryonic kidney cells, human embryonic retina cells and many others.

A method comprising introducing a nucleic acid or construct disclosed herein into a host cell is also described. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The nucleic acid may or construct be integrated into the genome (e.g. chromosome) of the host cell. Integration may be promoted by inclusion of sequences that promote recombination with the genome, in accordance with standard techniques.

Isolated

This refers to the state in which conjugates of the invention, antibodies for use in the invention, or nucleic acid encoding such conjugates, will generally be in accordance with the present invention. Thus, conjugates of the present invention, antibodies for use in the invention, or nucleic acid encoding such conjugates may be provided in isolated and/or purified from the environment in which they are prepared (such as cell culture), in substantially pure or homogeneous form, or, in the case of nucleic acid, free or substantially free of nucleic acid other than the sequence encoding a polypeptide with the required function. Isolated members and isolated nucleic acids will be free or substantially free of material with which they are found in the environment in which they are prepared (e.g. cell culture) when such preparation is by recombinant DNA technology practised in vitro or in vivo. Specific conjugates and nucleic acids may be formulated with diluents or adjuvants and still for practical purposes be isolated—for example the members may be mixed with pharmaceutically acceptable carriers or diluents when used in therapy. Specific conjugates may be glycosylated, either naturally or by systems of heterologous eukaryotic cells (e.g. CHO or NSO (ECACC 85110503) cells, or they may be (for example if produced by expression in a prokaryotic cell) unglycosylated.

Heterogeneous preparations of conjugates may also be used in the invention. For example, such preparations may be mixtures of conjugates comprising antibody molecules with full-length heavy chains and heavy chains lacking the C-terminal lysine, with various degrees of glycosylation and/or with derivatized amino acids, such as cyclization of an N-terminal glutamic acid to form a pyroglutamic acid residue.

Fibronectin

Fibronectin is an antigen subject to alternative splicing, and a number of alternative isoforms of fibronectin are known, including alternatively spliced isoforms A-FN and B-FN, comprising domains ED-A or ED-B respectively, which are known markers of angiogenesis. An antibody molecule, as referred to herein, may selectively bind to isoforms of fibronectin selectively expressed in the neovasculature. An antibody molecule may bind fibronectin isoform A-FN, e.g. it may bind domain ED-A (extra domain A). An antibody molecule may bind ED-B (extra domain B).

Fibronectin Extra Domain-A (ED-A or ED-A) is also known as ED, extra type III repeat A (EIIIA) or EDI. The sequence of human ED-A has been published by Kornblihtt et al. (1984), Nucleic Acids Res. 12, 5853-5868 and Paolella et al. (1988), Nucleic Acids Res. 16, 3545-3557. The sequence of human ED-A is also available on the SwissProt database as amino acids 1631-1720 (Fibronectin type-III 12; extra domain 2) of the amino acid sequence deposited under accession number P02751. The sequence of mouse ED-A is available on the SwissProt database as amino acids 1721-1810 (Fibronectin type-III 13; extra domain 2) of the amino acid sequence deposited under accession number P11276.

The ED-A isoform of fibronectin (A-FN) contains the Extra Domain-A (ED-A). The sequence of the human A-FN can be deduced from the corresponding human fibronectin precursor sequence which is available on the SwissProt database under accession number P02751. The sequence of the mouse A-FN can be deduced from the corresponding mouse fibronectin precursor sequence which is available on the SwissProt database under accession number P11276. The A-FN may be the human ED-A isoform of fibronectin. The ED-A may be the Extra Domain-A of human fibronectin.

ED-A is a 90 amino acid sequence which is inserted into fibronectin (FN) by alternative splicing and is located between domain 11 and 12 of FN (Borsi et al. (1987), J. Cell. Biol., 104, 595-600). ED-A is mainly absent in the plasma form of FN but is abundant during angiogenesis, embryogenesis, tissue remodeling, fibrosis, cardiac transplantation and solid tumour growth.

Fibronectin isoform B-FN is one of the best known markers angiogenesis (U.S. Ser. No. 10/382,107, WO01/62298). An extra domain "ED-B" of 91 amino acids is found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues.

Tenascin C

Tenascin-C is a large hexameric glycoprotein of the extracellular matrix which modulates cellular adhesion. It is involved in processes such as cell proliferation and cell migration and is associated with changes in tissue architecture as occurring during morphogenesis and embryogenesis as well as under tumourigenesis or angiogenesis. Several isoforms of tenascin-C can be generated as a result of alternative splicing which may lead to the inclusion of (multiple) domains in the central part of this protein, ranging from domain A1 to domain D (Borsi L et al Int J Cancer 1992; 52:688-692, Carnemolla B et al. Eur J Biochem 1992; 205:561-567, WO2006/050834). An antibody molecule, as referred to herein, may bind tenascin-C. An antibody molecule may bind tenascin-C domain A1.

Autoimmune Diseases

An autoimmune disease is preferably associated with and/or characterised by angiogenesis. An autoimmune disease may be an autoimmune disease characterised by angiogenesis, wherein the neovasculature expresses the ED-A isoform of fibronectin, the ED-B isoform of fibronectin and/or tenascin C. The autoimmune disease may be an inflammatory autoimmune disease, i.e. an autoimmune disease associated with and/or characterised by inflammation.

The conjugate used in the treatment of an autoimmune disease, or delivery of IL22 to sites of autoimmune disease in a patient, may be selected based on the expression of the ED-A isoform of fibronectin, ED-B isoform of fibronectin and/or tenascin C in said autoimmune disease. The autoimmune disease may be selected from the group consisting of: inflammatory bowel disease (IBD), atherosclerosis, rheumatoid arthritis (RA), multiple sclerosis (MS), endometriosis, autoimmune diabetes (such as diabetes mellitus type 1), psoriasis, psoriatic arthritis, and periodontitis. Preferably, the autoimmune disease is IBD.

IBD is a group of inflammatory conditions that affect the colon and small intestine. The major types of IBD are Crohn's disease (CD) and ulcerative colitis (UC), while other types of IBD include collagenous colitis, lymphocytic colitis, ischaemic colitis, diversion colitis, Behget's disease and indeterminate colitis. CD can affect any part of the gastrointestinal tract, whereas UC is typically restricted to the colon and rectum.

IBD, as referred to herein, may be CD, UC, collagenous colitis, lymphocytic colitis, ischaemic colitis, diversion colitis, Behget's disease or indeterminate colitis. In particular, the terms CD, UC, collagenous colitis, lymphocytic colitis, ischaemic colitis, diversion colitis, Behget's disease and indeterminate colitis, as used herein, may refer to active CD, active UC, active collagenous colitis, active lymphocytic colitis, active ischaemic colitis, active diversion colitis, and active indeterminate colitis, respectively. In one embodiment, the IBD may be CD or UC.

Inflammatory Diseases and/or Disorders

"Inflammatory disease and/or disorder" refers to disease and/or disorders which are accompanied and/or characterised by inflammation. An inflammatory disease and/or disorder is preferably associated with and/or characterised by angiogenesis. An inflammatory disease and/or disorder may be an inflammatory disease and/or disorder characterised by angiogenesis, wherein the neovasculature expresses the ED-A isoform of fibronectin, the ED-B isoform of fibronectin and/or tenascin C.

The conjugate used in the treatment of an inflammatory disease and/or disorder, or delivery of IL22 to sites of an inflammatory disease and/or disorder in a patient, may be selected based on the expression of the ED-A isoform of fibronectin, ED-B isoform of fibronectin and/or tenascin C in said inflammatory disease and/or disorder. The inflammatory disease and/or disorder may be selected from the group consisting of: graft versus host disease; wound healing; and ulcers, in particular diabetic foot ulcers.

Treatment

It is expected that the conjugates of the invention will have anti-inflammatory activity and thus find application in the treatment of inflammation and/or autoimmune diseases. Without being limited by any theoretical explanation, it is expected that the conjugates of the invention will show potent anti-inflammatory activity as a result of excellent targeting of neovasculature, as demonstrated in the examples. The conjugates of the present invention are thus designed to be used in methods of treatment of patients, preferably human patients.

Accordingly, the invention provides methods of treatment comprising administration of a conjugate according to the present invention, pharmaceutical compositions comprising such conjugates, and use of such a conjugates in the manufacture of a medicament for administration, for example in a method of making a medicament or pharmaceutical composition comprising formulating the conjugate with a pharmaceutically acceptable excipient. Pharmaceutically acceptable vehicles are well known and will be adapted by the person skilled in the art as a function of the nature and of the mode of administration of the active compound(s) chosen.

Conjugates according to the present invention will usually be administered in the form of a pharmaceutical composition, which may comprise at least one component in addition to the antibody molecule. Thus, pharmaceutical compositions described herein, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be by injection, e.g. intravenous or subcutaneous. Preferably, the conjugate of the present invention is administered intravenously.

Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be employed, as required. Many methods for the preparation of pharmaceutical formulations are known to those skilled in the art. See e.g. Robinson ed., Sustained and Controlled Release Drug Delivery Systems, Marcel Dekker, Inc., New York, 1978.

A composition comprising a conjugate according to the present invention may be administered alone or in combination with other treatments, concurrently or sequentially or as a combined preparation with another therapeutic agent or agents, for the treatment of inflammation and/or an autoimmune disease. For example, a conjugate of the invention may be used in combination with an existing therapeutic agent for inflammation and/or an autoimmune disease.

A conjugate according to the invention may be used in the manufacture of a medicament. The medicament may be for separate or combined administration to an individual, and accordingly may comprise the conjugate and the additional component as a combined preparation or as separate preparations. Separate preparations may be used to facilitate separate and sequential or simultaneous administration, and allow administration of the components by different routes.

In accordance with the present invention, compositions provided may be administered to mammals, preferably humans. Administration may be in a "therapeutically effective amount", this being sufficient to show benefit to a patient. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of conjugate, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of antibody are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for the type of medicament being administered, may be used. A therapeutically effective amount or suitable dose of a conjugate for use in the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the conjugate. A typical conjugate dose will be in the range 100 μg to 1 g for systemic applications. An initial higher loading dose, followed by one or more lower doses, may be administered. This is a dose for a single treatment of an adult patient, which may be proportionally adjusted for children and infants, and also adjusted according to conjugate format in proportion to molecular weight. Treatments may be repeated at daily, twice-weekly, weekly or monthly intervals, at the discretion of the physician. Treatments may be every two to four weeks for subcutaneous administration and every four to eight weeks for intravenous administration. In some embodiments of the present invention, treatment is periodic, and the period between administrations is about two weeks or more, e.g. about three weeks or more, about four weeks or more, or about once a month. In other embodiments of the invention, treatment may be given before, and/or after surgery, and may be administered or applied directly at the anatomical site of surgical treatment.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Materials and Methods
Cloning of Fusion Proteins Comprising IL22 and Anti-ED-A antibody F8

The genes encoding the antibody fusion proteins comprising muIL22 (from mus musculus) or human IL22 and anti-ED-A antibody F8 were generated using PCR assembly. The sequence encoding IL22 (lacking the signal peptide sequence) was linked via a sequence encoding a 15 amino acid glycine-serine-linker [$(G_4S)_3$] either to the C-terminus (F8-IL22) or the N-terminus (IL22-F8) of the gene encoding the F8 antibody in diabody format (heavy chain and light connected via a GGSGG-linker). A sequence encoding an IgG-derived signal peptide was added at the N-terminus to enable high yield production of the encoded fusion proteins.

The genes encoding the antibody fusion proteins comprising muIL22, were cloned into the pcDNA 3.1 mammalian cell expression vector using engineered NheI and NotI restriction sites. The genes encoding the antibody fusion proteins comprising huIL22 were generated by PCR assembly and inserted into the EcoRI and SpeI restriction sites of the pMM-124 mammalian cell expression vector.

Figure 1B:
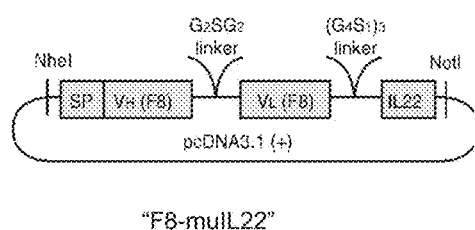
Figure 1C:
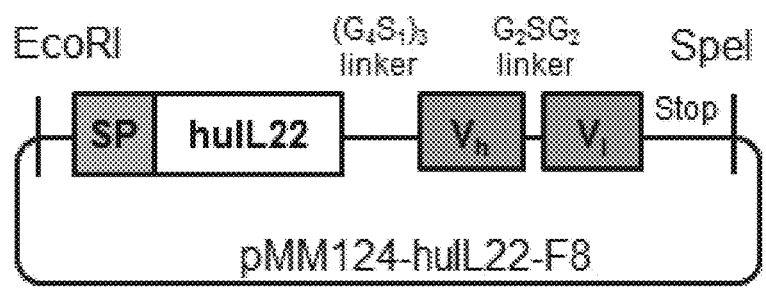

A schematic illustration of the gene assembly for the antibody fusion proteins comprising muIL22 is shown in FIGS. 1 A and B, while FIG. 1C shows gene assembly for the huIL22-F8 antibody fusion protein.

The sequences of the genes used to encode the muIL22-F8 and F8-muIL22 fusion proteins are shown in SEQ ID NOs: 21 and 22, respectively, while the amino acid sequences of the mature muIL22-F8 and F8-muIL22 fusion proteins employed in the experiments reported below are shown in SEQ ID NOs: 23 and 24, respectively. The sequences of the genes used to encode the huIL22-F8 and F8-huIL22 fusion proteins are shown in SEQ ID NOs: 14 and 15, respectively, while the amino acid sequences of the mature huIL22-F8 and F8-huIL22 fusion proteins employed in the experiments reported below are shown in SEQ ID NOs: 16 and 17, respectively. The signal peptides are cleaved after expression of the fusion proteins and thus are not part of the mature fusion proteins.

Expression of Fusion Proteins
Fusion Proteins Comprising IL22

Fusion proteins comprising muIL22 were expressed transiently in CHO-S cells via PEI mediated transfection. 500× $10^6$ cells were resuspended in 250 mL of pre-warmed ProCHO-2 medium (supplemented with 10% FBS, 2% HT supplement, 4% Ultraglutamine, 1% antibiotics-antimycotics solution). 625 μg of plasmid containing the gene encoding the fusion protein was diluted with a sterile 150 mM solution of NaCl to reach a total volume of 12.5 ml. 2.5 mL of sterile PEI solution (polyethylenimine, 1 g/L linear, MW 25'000) in filtered water was mixed with 10 ml sterile 150 mM NaCl. The PEI mixture was added to the plasmid mixture and incubated for 10 minutes at room temperature. After the required incubation time, the mixture was added to the prepared cells and the cells were placed on a 37° C. shaker at 160 rpm for 4 hours. After 4 hours 250 mL of prewarmed PowerCHO-2 medium (supplemented with 10% FBS, 2% HT supplement, 4% Ultraglutamine, 1% antibiotics-antimycotics solution) was added and the cells were placed on a 31° C. shaker at 140 rpm for 6 days. This was followed by purification of the fusion protein.

Fusion proteins comprising huIL22 were prepared similarly to the fusion proteins comprising muIL22, by transient gene expression in suspension adapted CHO-S cell cultures. Following transfection cells were maintained in PowerCHO-2 medium (supplemented with 2% HT supplement, 4 mM Ultraglutamine and 1% antibiotics-antimycotics solution) for 6 days at 31° C. under shaking conditions, after which the culture supernatant was harvest by centrifugation and further processed to purify the fusion protein.

Purification of Fusion Proteins Using Protein A Resin 500 mL of transfected CHO-S cell suspension was centrifuged for 20 minutes at 7000 rpm at 4° C. The supernatant was decanted into a flask and stored at 4° C. and the pellet discarded. The supernatant was loaded over a column containing gel filtration medium (Sephadex™ G-25 Medium, GE Healthcare, #17-0033-02) onto a column containing protein A resin (protein A agarose beads/resin, Sino Biological Inc.), using a pump of which the flow rate had been adjusted to a maximum of 2 mL/minute using PBS. The gel filtration resin was subsequently discarded. The protein A column was washed with 400 mL of "wash A" (100 mM NaCl (Sodium chloride for analysis, Emsure™, 7547-14-5), 0.5 mM EDTA pH 8.0 (kindly provided by Franziska Bootz), 0.1% Tween 20 (Polyoxyethylenesorbitan monolaurate, Sigma-Aldrich™, # SZBA3190V) in PBS) until the optical density of the wash as determined with a spectrophotometer (NanoDrop 2000 c, witec ag, OD280 nm) was below 0.1 and then washed with 400 mL of "wash B" (100 mM NaCl 0.5 mM EDTA in PBS) until the optical density at 280 nm of the wash as determined with the spectrophotometer NanoDrop was below 0.05. The fusion protein comprising muIL22 was eluted by gravity flow with 10 mL of 0.1 M glycine (pH3, Fluka™, # BCBB2819). The fractions were collected as 1 mL aliquots in 1.5 mL Eppendorf tubes and immediately put on ice. Fractions containing the fusion protein, as confirmed by UV spectrometry, were pooled, transferred into a dialysis membrane (Spectra/Por™ Dialysis Membrane, MWCO 12'000-14'000, Spectrum laboratories) and dialysed overnight in 3-4 L of PBS. The next day the fusion protein solution was transferred to an Eppendorf tube and stored at 4° C. for 1-2 days for further analysis or snap frozen in liquid nitrogen and transferred to a −80° C. freezer. The same method could be used to purify fusion proteins comprising huIL22.

Deglycosylation of Fusion Proteins

Deglycosylation of fusion proteins comprising muIL22 was performed using Peptide-N-Glycosidase F (PNGase F, NEB P0704S) to remove complex oligosaccharides from N-linked glycoproteins. Under denaturing conditions 15 µg of fusion protein were incubated with 10× Glycoprotein Denaturing Buffer (NEB) in a total volume of 30 µl for 10 minutes at 99° C. The denatured fusion protein was mixed with 6 µl 10× Glycobuffer 2 (NEB), 6 µl of 10% NP-40 and deionized water in a total volume of 60 µl. After addition of 3 µl PNGase F the reaction mix was incubated for 4 hours at 37° C. Afterwards all samples were analyzed by SDS-PAGE. The effect of deglycosylation is visible as mobility shift and sharpening of bands in SDS-PAGE gels. Deglycosylation of fusion proteins comprising huIL22 could be performed in the same way.

Size Exclusion Chromatography of Fusion Proteins

Size exclusion chromatography of fusion proteins was performed using a superdex 200 5/150 column (GE healthcare) with phosphate buffered saline as running buffer on a ÄKTA-FPLC system (GE healthcare). 100 µl protein solutions were injected into a loop and automatically injected onto the column. UV absorbance at 280 nm was assessed over time.

Biacore Analysis of Fusion Proteins

Using surface plasmon resonance (Biacore 3000 system, GE Healthcare) the binding affinity of fusion proteins comprising muIL22 to ED-A was analysed. A microsensor chip (CM5, GE Healthcare) was coated with 11A12, a recombinantly expressed ED-A, with 1500 resonance units coating density. For analysis on surface plasmon resonance, proteins were filtered with a syringe driven filter unit (Millex®-GV, Low protein binding durapore membrane, 0.22 µm, # N3HA70695) and their concentration determined with a spectrophotometer (NanoDrop 2000c, witec ag, OD280 nm). Biacore analysis of fusion proteins comprising huIL22 could be performed in the same way.

ELISA of Fusion Proteins

The binding capacity of the antibody moiety was further confirmed by ELISA. Recombinant EDA-domain was immobilized on maxisorp wells (Nunc-Immuno) over night at room temperature. On the day of binding assessment, wells were blocked using 200 µl 4% milk in phosphate buffered saline solution (milk-PBS) for 2 hours at room temperature. After removal of the blocking solution, 200 µl of different antibody concentrations in 2% milk-PBS were added to the wells and incubated for 1 hour at room temperature. Afterwards wells were washed with three times 200 µl PBS containing 0.1% Tween-20 and three times PBS. Subsequently, 200 µl 2% milk-PBS containing protein-A HRP (GE healthcare) were added to each well. After 40 minutes incubation at room temperature, plates were washed three times with 0.1% PBS-Tween and PBS alone after which the POD substrate (Roche) was added. The reaction was stopped using H2SO4 and the read out was obtained measuring absorption at 450 nm and 650 nm using a UV spectrophotometer (SpectraMax Paradigm, Molecular Devices)

Bioactivity Assay of Fusion Proteins: IL22 Induced Phosphorylation of STAT3

The activity of muIL22 in the muIL22 containing fusion proteins was verified by STAT3 phosphorylation in HT29cells. Cells were incubated with the fusion proteins and phosphorylation of STAT3 was quantified by Western Blot analysis.

Figure 4:
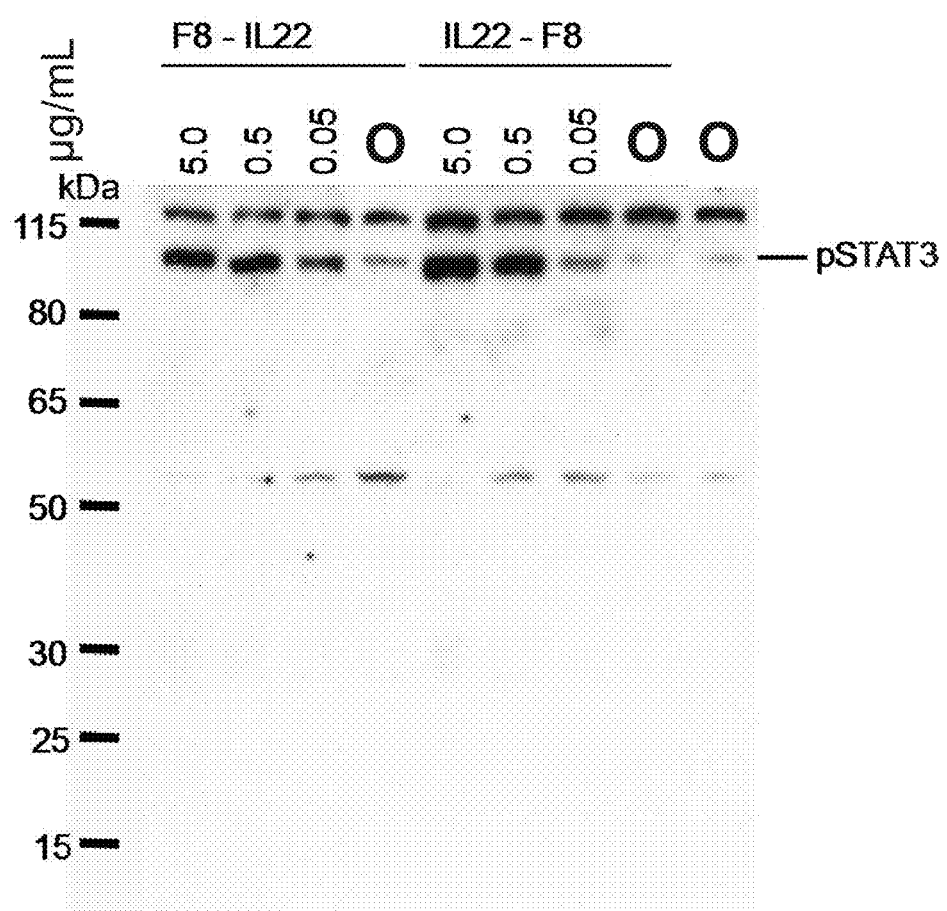
FIG. 4 is a photograph showing the results of a bioactivity assay using the F8-muIL22 and muIL22-F8 fusion proteins and demonstrates that the muIL22 in the F8-muIL22 and muIL22-F8 fusion proteins retains the ability to induce phosphorylation of STAT3 upon binding to the receptor on colon carcinoma cells. The concentration of the fusion proteins employed in the experiments (5 µg/ml, 0.5 µg/ml, and 0.05 µg/ml) is indicated at the top of the figure. "0" indicates the lane comprising the negative control. The location of the band corresponding to phosphorylated STAT3 is indicated.

HT29 cells were seeded with a density of $0.1 \times 10^6$ cells per well in 300 µl of McCoy's medium (GIBCO, supplemented with 10% FBS and 1% antibiotics-antimycotics solution) in a sterile 96 well plate. When cells were attached to the flask, the medium was replaced by serum-free medium and cells were incubated over night at 37° C. The following day, muIL22 fusion proteins were added in a ten-fold serial dilution and starting with a concentration of 5 µg/ml as shown in FIG. 4. After an incubation period of 20 minutes at 37° C., cells were washed with wash buffer (10 ml PBS containing 1 tablet protease inhibitor (Roche, Complete Mini EDTA-free protease inhibitor cocktail)) and 20 μl RIPA buffer (25 mM TrisHCl pH 7.4, 150 mM NaCl, 1% NP40, 0.1% SDS), 1 tablet protease inhibitor was added to the cells for cell lysis. After centrifugation (2000 rpm, 15 min, 25° C.), the cell lysate was used for SDS-PAGE. Afterwards the separated proteins were blotted from the polyacrylamid gel onto a nitrocellulose membrane for 1 h at 30 V and 220 mA. Following this, the membrane was blocked in 4% milk PBS for 1 h at 25° C. A 1:1000 dilution of the primary antibody, mouse-α-human-phospho-STAT3 (Peprotech, 0.1 mg/ml), in 2% milk PBS was added to the membrane and incubated for 1 h at 25° C. on a shaker. Before incubation with the secondary antibody, a washing step was performed. The membrane was incubated three times for 5 minutes in PBS+0.1% Tween. The secondary antibody, α-mouse-horseradish peroxidase (Invitrogen), was added to the membrane at a dilution of 1:1000 in 2% milk PBS and incubated for 1 hour at 25° C. on a shaker. After incubation with the secondary antibody, a washing procedure was performed with PBS+0.1% Tween for 5 minutes two times and afterwards two times with PBS for 5 minutes. For signal detection, the membrane was covered with ECL reagent (Amersham Prime, GE healthcare) and exposed to a film and then developed. The activity of huIL22 in fusion proteins comprising huIL22 could be determined in the same way.

Radiolabeling of muIL22 Fusion Proteins

For radiolabeling of fusion proteins comprising muIL22, the indirect IODO-GEN™ method was performed, using pre-coated iodination tubes (#28601, Pierce). 150 μg of protein in 400 μl PBS were labeled with 200 μCi of Natriumiodid 125 (NaI 125; # NEZ033A002MC, Perkin Elmer) as follows.

A pre-coated iodination tube was washed with 1 ml of PBS. After removal of the PBS, 100 μl of PBS were added directly to the bottom of the tube and mixed with the respective amount of NaI 125. The mix was incubated for 5 minutes while slightly swirling the tube every 30 seconds. 100 μl of activated iodine were added to 150 μg of the fusion protein to be labeled in a volume of 400 μl PBS and again incubated for 5 minutes while slightly swirling every 30 seconds. The labeled fusion protein was loaded onto a PD-10 column (#17-0851-01, GE Healthcare), previously blocked with 1 mg/ml BSA. Immediately after absorption of the fusion protein onto the PD-10 column, 2 ml of PBS were added to reach the total volume of the column. Elution of the fusion protein was performed with 3 ml PBS and 5 fractions of the fusion protein were collected.

To determine the amount of radiolabel incorporated into the fusion protein, 5 μl of the input and 5 μl of each fraction were diluted in 1 ml of PBS and out of this an additional 1:100 dilution was prepared in radiation counter tubes (#55.470, Sarstedt). The radioactivity of each dilution was measured using a radiation counter (Cobra Autogamma, Packard). The results were used to calculate which fraction contained the highest concentration of radiolabeled fusion protein and to determine the efficiency with which the radiolabel was incorporated into the fusion protein.

Specifically, the 1:100 dilutions were made as a control of linearity. The input fraction gives a value for the radioactivity input used. The sum of the radioactivity measurements of the fractions allows the incorporation efficiency to be determined (incorporation=Σfractions/input). It is further assumed that all proteins elute in the fractions collected. Therefore, besides the incorporation efficiency, the amount of protein present in each fraction can be calculated. The percentage radioactivity present in a fraction, as calculated using the radioactivity measurement for said fraction divided by the sum of radioactivity in all fractions, reflects the percentage of protein from the protein input present in said fraction. Using these measurements, it was therefore possible to determine the protein concentration present in a particular fraction, which—in turn—allowed the volume, which had to be injected into a mouse in order to administer the required amount of radiolabeled fusion protein to be determined.

Tumour Targeting Using the muIL22-F8 and F8-muIL22 Fusion Proteins

The in vivo targeting performance of fusion proteins comprising muIL22 was assessed by quantitative biodistribution studies in F9 tumour bearing mice. Antibody conjugates were labeled with $^{125}$I using the indirect IODO-GEN™ method as described above. 15 μg of radioiodinated fusion protein was injected intra venously (i.v.) into the lateral tail vein. Mice were sacrificed 24 h after injection, organs were excised, weighed and radioactivity was measured using a Packard Cobra γ counter. Radioactivity of organs was expressed as percentage of injected dose per gram of tissue (% ID/g±SEM). The same approach could be used to determine the in vivo targeting performance of fusion proteins comprising human IL22 (huIL22).

Autoradiographic Analysis of Conjugate Localization in a Mouse Model of Ulcerative Colitis To induce ulcerative colitis (a type of IBD) in mice, a concentration of 2.0%, 2.5%, or 3.0% DSS in drinking water was administered to the mice for 5 days. At day 5, drinking water was changed to water supplemented with 0.25% NaHCO$_3$ and 5% Glucose for seven days. Mice were weighed daily and scored for disease severity. When weight loss exceeded 10%, 200 μl of 0.9% NaCl (Braun) were subcutaneously injected into the mice. When weight loss exceeded 15%, and occurred in combination with diarrhea, mice received a subcutaneous injection of 200 μl of 0.9% NaCl and 200 mg/kg metamizol (Buscopan compositum, Boehringer Ingelheim).

Twelve days after starting the induction of DSS-induced colitis, mice which had received 2.0% DSS in drinking water were used as (non-injected) control mice, mice which had received 2.5% DSS in drinking water, were injected intravenously in the lateral tail vein with 15 μg of muIL22-F8 or F8-muIL22 radiolabeled with $^{125}$I, and mice which had received 3.0% DSS and developed the most severe colitis as measured by disease score and weight loss were injected intravenously in the lateral tail vein with 15 μg of $^{125}$I radiolabeled KSF-muIL22 or muIL22-KSF.

Twenty four hours after injection of the radiolabeled immunocytokine, mice were sacrificed and small and large intestine (washed with PBS), mesenteric and inguinal lymph nodes and liver were exposed to a phosphorimaging plate (Fujifilm Holdings Corporation, Tokyo, Japan) for 13 hours.

Therapy of DSS-Induced Ulcerative Colitis with muIL22-F8 Fusion Protein

To induce ulcerative colitis in mice, a concentration of 3.0% DSS in drinking water was administered for 5 days. At day 5 drinking water was changed to water supplemented with 0.25% NaHCO$_3$ and 5% Glucose for seven days. Mice were weighed daily and scored for disease severity. When weight loss exceeded 10%, 200 μl of 0.9% NaCl (Braun) were injected subcutaneously into the mice. When weight loss exceeded 15%, and occurred in combination with diarrhea, mice received a subcutaneous injection of 200 μl of 0.9% NaCl and 200 mg/kg metamizol (Buscopan compositum, Boehringer Ingelheim). Disease severity in mice was scored with respect to stool consistency, faecal blood and mouse appearance.

At day 5, mice were classified according to consumption of DSS containing drinking water (not all mice drank the same amount of DSS containing drinking water), weight loss and disease score and divided into two groups of ten mice to receive either 100 μg of muIL22-F8 or PBS (as a control) at day six, eight, ten, twelve and fourteen.

Results

Characterization of muIL22-F8 and F8-muIL22 Fusion Proteins

Figure 2A:
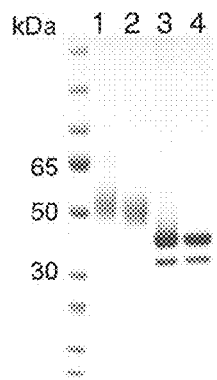
FIGS. 2A-2B are photographs showing the results of an SDS-PAGE analysis of the muIL22-F8 and F8-muIL22 conjugates, respectively, under reducing and non-reducing conditions (lanes 1 and 2, respectively), and in the presence of PNGase F (lanes 3 and 4, respectively).
Figure 2B:
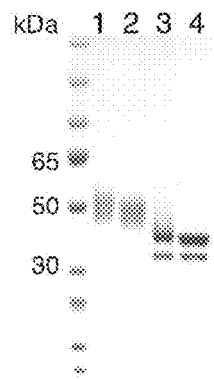
Figure 2C:
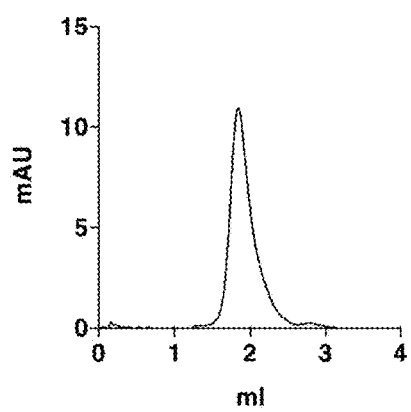
FIGS. 2C-2D are graphs showing the results of size exclusion chromatography of the muIL22-F8 and F8-muIL22 conjugates, respectively. The fact that only single peaks were visible confirms the homogeneity of the conjugate preparations.
Figure 2D:
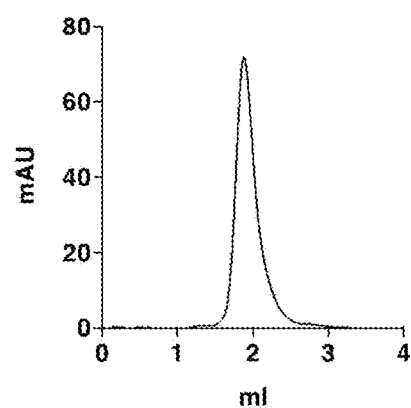

The purified fusion proteins exhibited favourable biochemical properties as confirmed using (1) SDS-PAGE and (2) size exclusion chromatography. SDS-PAGE analysis using coomassie staining revealed broad protein bands slightly higher than the estimated 44 kDa (FIGS. 2A and B). This shift was caused by the presence of N-linked glycans, which could be removed using PNGase F, leading to a band shift to the expected size for the fusion proteins (FIGS. 2A and B). Size exclusion chromatography analysis using a Superdex S200 5/150 column further confirmed the homogeneity of the conjugate preparations (FIGS. 2C and D).

After fusion with muIL22, the binding capacity of the F8 moiety to the ED-A of fibronectin was maintained, as confirmed using surface plasmon resonance (Biacore) (FIGS. 3 A and B) and ELISA analysis (FIGS. 3 C and D).

The muIL22 also retained its biological activity after fusion with the F8 antibody in the muIL22-F8 and F8-muIL22 fusion proteins, as determined using western blot analysis on of phosphorylated STAT3 in HT29 cells after induction using the muIL22 fusion proteins (FIG. 4).

Tumor Targeting Using the muIL22-F8 and F8-muIL22 Fusion Proteins

Figure 5A:
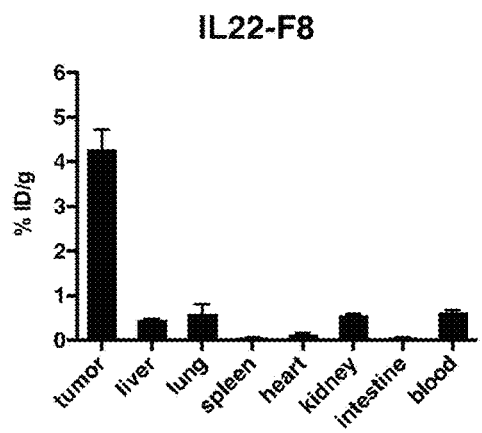
FIGS. 5A-5B are graphs showing the results of tumour targeting studies using the muIL22-F8 and F8-muIL22 fusion proteins, respectively, in F9 tumour-bearing mice. The fusion proteins primarily localized to the tumour tissue, which is known to express ED-A in the tumour neovasculature, with minimal amounts of fusion protein found in other (healthy) tissues of the mice, which are not expected to express ED-A. The y-axis shows the percentage of the injected dose of the fusion protein per gram of tissue (% ID/g).
Figure 5B:
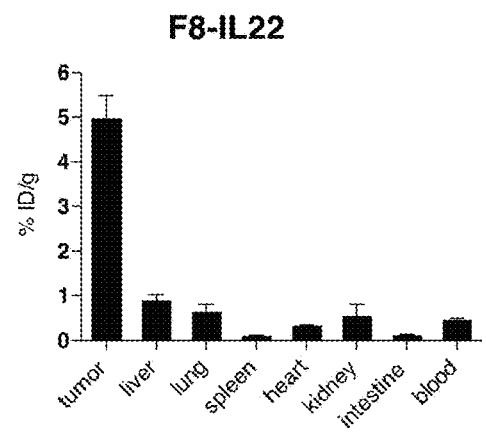

Quantitative biodistribution studies of the muIL22-F8 and F8-muIL22 fusion proteins in F9 tumour bearing mice showed excellent tumour targeting by the fusion proteins (FIG. 5). Although the fusion proteins are not intended for use in treating or detecting tumours, this demonstrates that the fusion proteins specifically target tissues expressing ED-A (such as neovasculature, which is known to express ED-A), with very limited presence of the fusion proteins in other (healthy) tissues. These excellent targeting properties are expected to be useful when employing fusion proteins comprising IL22 for therapeutic applications.

Figure 6:
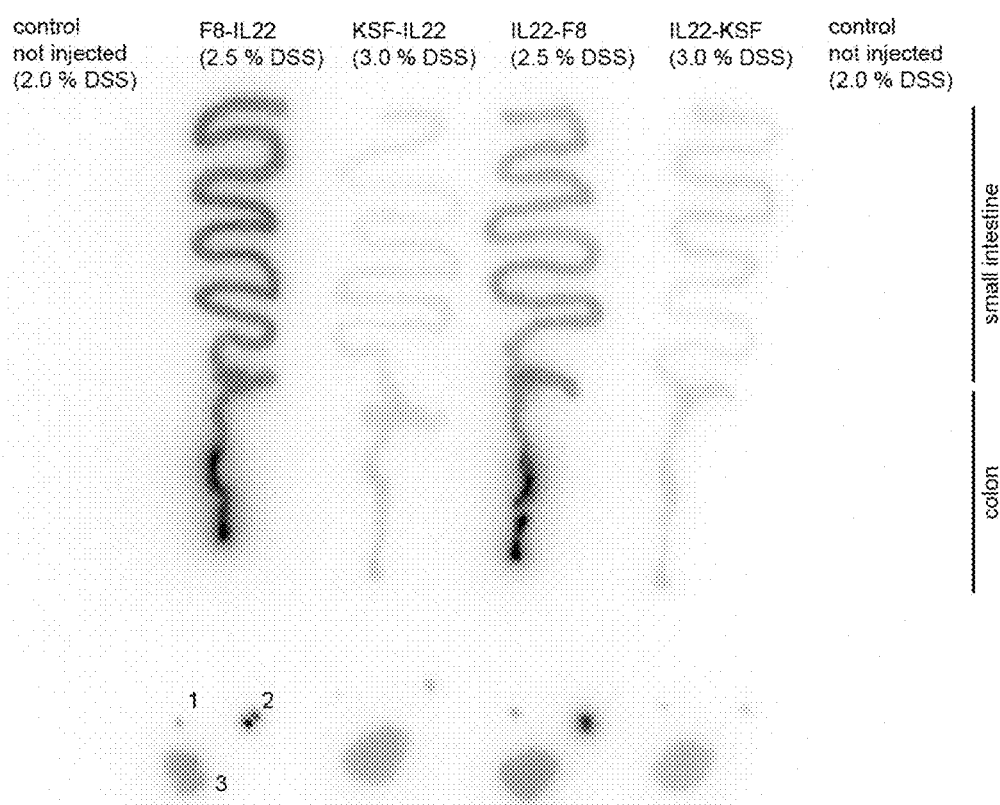
FIG. 6 is a photograph showing the ex-vivo autoradiographic analysis of the targeting effect of F8 and KSF antibodies fused to muIL22 in mice with colitis. When muIL-22 was fused to the control antibody KSF, no specific uptake in the colon was visible. When muIL-22 was fused to the anti-EDA antibody, F8, specific localization of the antibody to the terminal, and most inflamed part, of the colon was visible. Surprisingly, when muIL22 was fused to the N-terminus of the F8 antibody (muIL22-F8), the specificity with which the conjugate localized to the inflamed part of the colon (signal intensity ratio of inflamed colonic lesions to uninflamed jejunum) was 5.4-fold higher compared with the specificity exhibited by the conjugate in which muIL22 was fused to the C-terminus of the F8 antibody (F8-muIL22). In the autoradiograph at the bottom of FIG. 6, 1=inguinal lymph node, 2=mesenteric lymph node, 3=liver.

Autoradiographic Analysis of Conjugate Localization in a Mouse Model of Ulcerative Colitis Organs of non-injected animals did not yield any signal and organs of mice injected with either radiolabeled KSF-muIL22 or muIL22-KSF showed only a slight background signal, which is believed to result from the injection of a radioactive substance rather than being due to any targeting by tese fusion proteins (FIG. 6). A strong signal in inflamed lesions, however, was detected in colons derived from mice injected with radiolabeled muIL22-F8 or F8-muIL22, in particular at the most inflamed, terminal, part of the colon, whereas almost no signal was detectable in the small intestine of these animals (FIG. 6).

Figure 7:
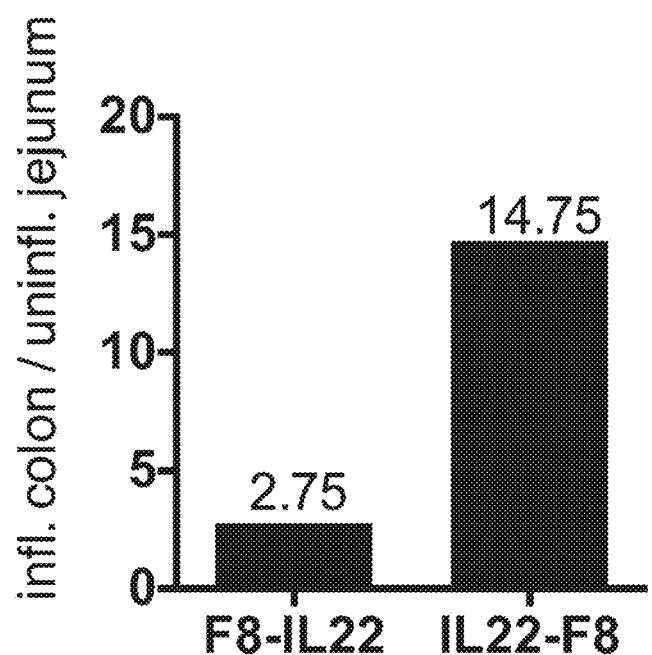
FIG. 7 is a graph showing the signal intensity in inflamed colonic lesions to uninflamed jejunum observed with the muIL22-F8 and F8-muIL22 conjugates. The signal ratio was 5.4-fold higher in the colon derived from a mouse injected with a conjugate in which muIL22 was fused to the N-terminus of the targeting antibody, F8 (muIL22-F8) than with a conjugate in which muIL22 was fused to the C-terminus of the targeting antibody (F8-muIL22). This data clearly shows the superior targeting specificity of muIL22-F8 over F8-muIL22.

The signal intensity ratio of inflamed colon to small intestine demonstrated more selective targeting by muIL22-F8 than F8-muIL22 by a factor of 5.4 (FIG. 6, FIG. 7). Mesenteric lymph nodes of injected animals revealed a radioactive signal, whereas no signal was detectable in inguinal lymph nodes and liver of the same mice.

Therapy of DSS-Induced Colitis with muIL22-F8 Fusion Protein

Figure 8:
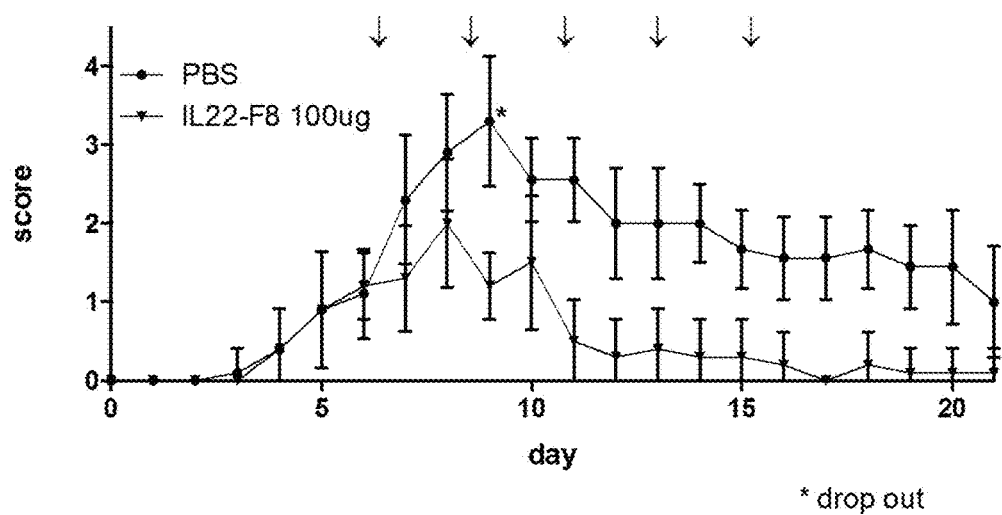
FIG. 8 is a graph showing a plot of the disease score in mice with DSS induced colitis comparing i.v. administration (indicated by arrows) of muIL22 fused to the N-terminus of the F8 antibody (muIL22-F8), at a dose of 100 µg per injection, with saline. In this setting, muIL22-F8 treatment demonstrated more rapid disease recovery. In contrast to the saline group, no mice dropped out of the muIL22-F8 treatment group due to extreme severity of the disease.
Figure 9:
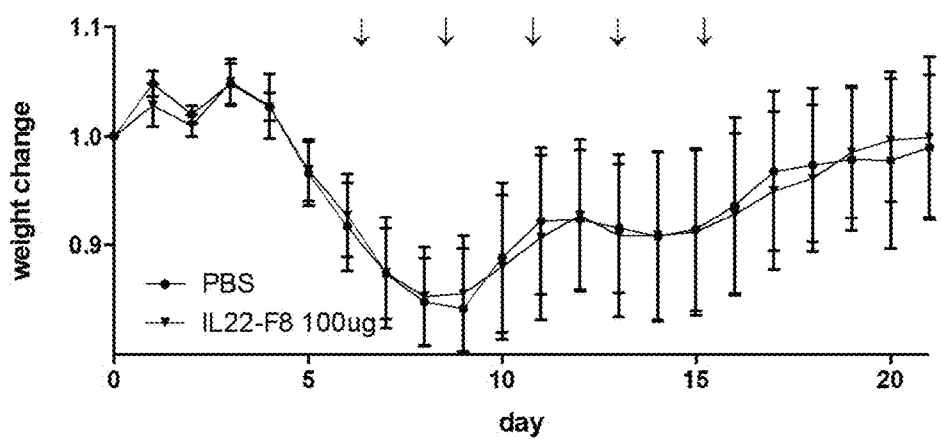
FIG. 9 is a graph showing the change in weight (weight divided by initial weight) in mice with DSS induced colitis comparing i.v. administration (indicated by arrows) of muIL22 fused to the N-terminus of the F8 antibody (muIL22-F8), at a dose of 100 µg per injection, with saline. No differences between the groups can be observed showing that muIL22-F8 treatment is well tolerated.

As shown in FIG. 8, mice treated with muIL22-F8 enjoyed a more rapid and sustained reduction in the disease score, than mice treated with PBS. In contrast to the PBS group, the muIL22-F8 treatment group did not report a drop out due to extreme severity of the disease. Monitoring of weight change further revealed no differences between the groups, confirming good tolerability of the treatment with muIL22-F8.

Characterization of huIL22-F8 Fusion Protein

Figure 2E:
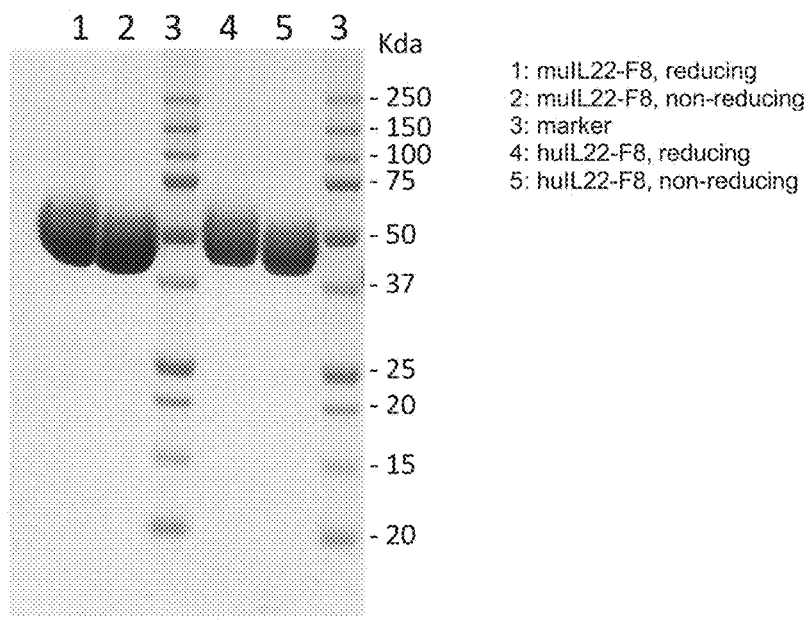
FIG. 2E is a photograph showing the results of an SDS-PAGE analysis of the muIL22-F8 and huIL22-F8 conjugates under reducing and non-reducing conditions (lanes 1 and 2, and 4 and 5, respectively.
Figure 2F:
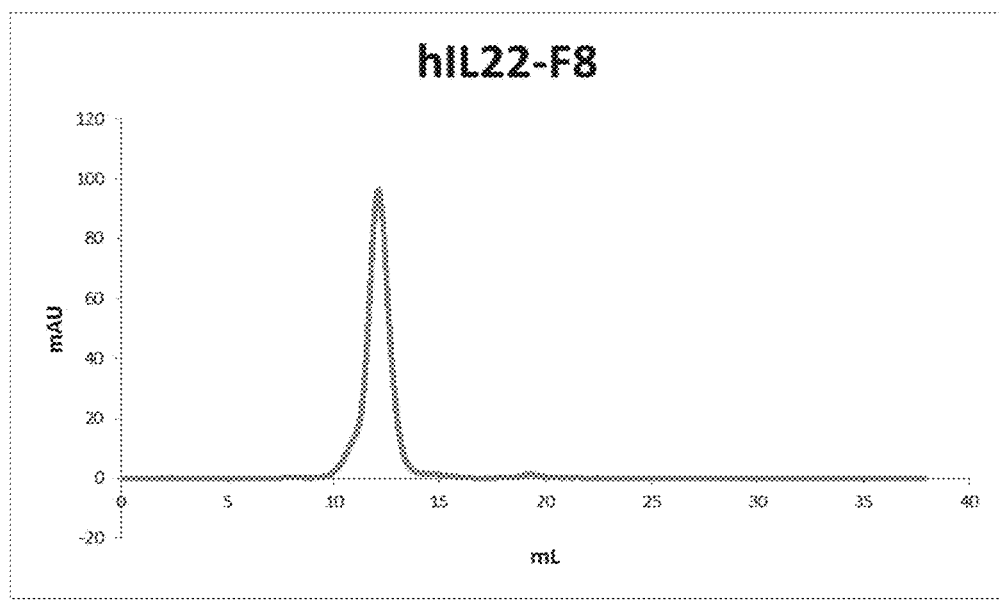
FIG. 2F is a graph showing the results of size exclusion chromatography of the huIL22-F8 conjugate. The single peak confirms the homogeneity of the conjugate preparation.
Figure 3A:
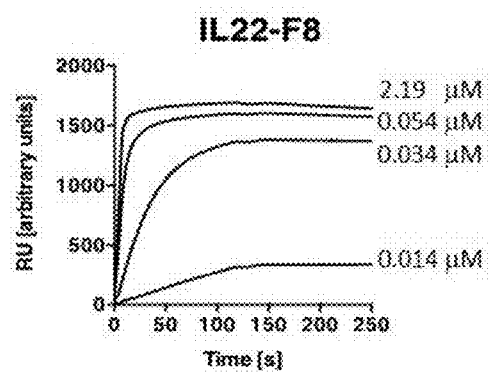
FIGS. 3A-3B are graphs showing the results of surface plasmon resonance (Biacore) using an ED-A coated chip and the muIL22-F8 and F8-muIL22 fusion proteins, respectively, and demonstrate that the muIL22-F8 and F8-muIL22 fusion proteins are capable of binding ED-A.
Figure 3B:
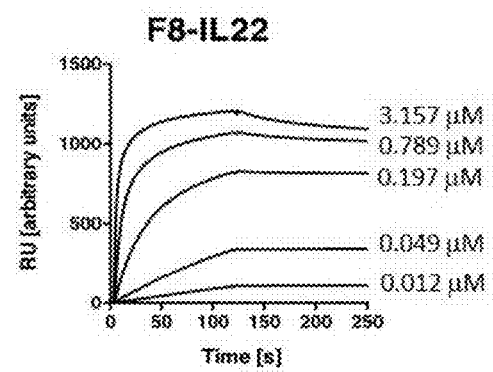
Figure 3C:
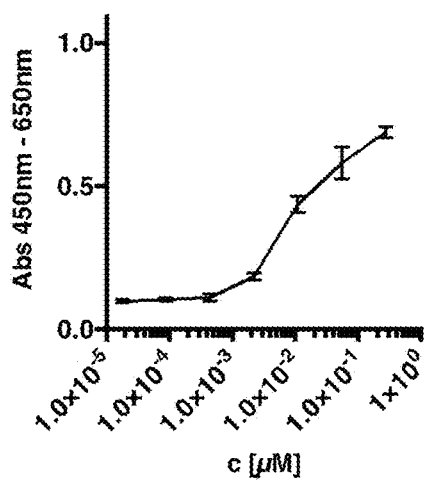
FIGS. 3C-3D are graphs showing the results of an ELISA using ED-A coated wells and the muIL22-F8 and F8-muIL22 fusion proteins, respectively, and further confirms that the muIL22-F8 and F8-muIL22 fusion proteins are capable of binding ED-A.
Figure 3D:
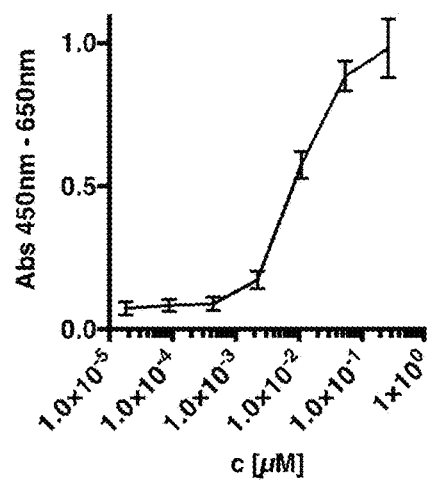

The purified fusion proteins exhibited favourable biochemical properties as confirmed using (1) SDS-PAGE and (2) size exclusion chromatography. SDS-PAGE analysis using coomassie staining revealed broad protein bands slightly higher than the estimated molecular weight due to glycosylation (FIG. 2 E). The molecular weights of the protein bands representing the huIL22-F8 and muIL22-F8 fusion proteins were the same (FIG. 2E). Size exclusion chromatography analysis using a Superdex S200 5/150 column further confirmed the homogeneity of the huIL22-F8 conjugate preparation (FIG. 2F).

Sequence Listing

```
Amino acid sequences of the F8 CDR's
                                        (SEQ ID NO: 1)
F8 CDR1 VH - LFT (SEQ ID NO: 2)
F8 CDR2 VH - SGSGGS (SEQ ID NO: 3)
F8 CDR3 VH - STHLYL (SEQ ID NO: 4)
F8 CDR1 VL - MPF (SEQ ID NO: 5)
F8 CDR2 VL - GASSRAT (SEQ ID NO: 6)
F8 CDR3 VL - MRGRPP Amino acid sequence of the F8 VH domain
                                        (SEQ ID NO: 7)
EVQLLESGGGLVQPGGSLRLSCAASGFTFSLFTMSWVRQAPGKGLEWVSA

ISGSGGSTYYADSVKGRFTISRDNSKNTLYLQMNSLRAEDTAVYYCAKST

HLYLFDYVVGQGTLVTVSS

Amino acid sequence of the F8 VL domain
                                        (SEQ ID NO: 8)
EIVLTQSPGTLSLSPGERATLSCRASQSVSMPFLAWYQQKPGQAPRLLIY

GASSRATGIPDRFSGSGSGTDFTLTISRLEPEDFAVYYCQQMRGRPPTFG

QGTKVEIK

Amino acid sequence of the linker linking the F8
VH domain to the F8 VL domain in the F8 diabody
                                        (SEQ ID NO: 9)
GGSGG Amino acid sequence of the F8 diabody
                                        (SEQ ID NO: 10)
EVQLLESGGGLVQPGGSLRLSCAASGFTFSLFTMSWVRQAPGKGLEWVSA

ISGSGGSTYYADSVKGRFTISRDNSKNTLYLQMNSLRAEDTAVYYCAKST

HLYLFDYVVGQGTLVTVSSGGSGGEIVLTQSPGTLSLSPGERATLSCRAS

QSVSMPFLAWYQQKPGQAPRLLIYGASSRATGIPDRFSGSGSGTDFTLTI

SRLEPEDFAVYYCQQMRGRPPTFGQGTKVEIK
```

```
Amino acid sequence of human IL22 (huIL22)
                                     (SEQ ID NO: 11)
APISSHCRLDKSNFQQPYITNRTFMLAKEASLADNNTDVRLIGEKLFHGV

SMSERCYLMKQVLNFTLEEVLFPQSDRFQPYMQEVVPFLARLSNRLSTCH

IEGDDLHIQRNVQKLKDTVKKLGESGEIKAIGELDLLFMSLRNACI
```

Amino acid sequence of the linker linking huIL22 to the F8 VH domain in the huIL22-F8 conjugate, and huIL22 to the F8 VL domain in the F8-huIL22 conjugate, respectively (SEQ ID NO: 12)
GGGGSGGGGSGGGGS

```
Nucleotide sequence encoding huIL22
                                     (SEQ ID NO: 13)
GCGCCCATCAGCTCCCACTGCAGGCTTGACAAGTCCAACTTCCAGCAGCC

CTATATCACCAACCGCACCTTCATGCTGGCTAAGGAGGCTAGCTTGGCTG

ATAACAACACAGACGTTCGTCTCATTGGGGAGAAACTGTTCCACGGAGTC

AGTATGAGTGAGCGCTGCTATCTGATGAAGCAGGTGCTGAACTTCACCCT

TGAAGAAGTGCTGTTCCCTCAATCTGATAGGTTCCAGCCTTATATGCAGG

AGGTGGTGCCCTTCCTGGCCAGGCTCAGCAACAGGCTAAGCACATGTCAT

ATTGAAGGTGATGACCTGCATATCCAGAGGAATGTGCAAAAGCTGAAGGA

CACAGTGAAAAAGCTTGGAGAGAGTGGAGAGATCAAAGCAATTGGAGAAC

TGGATTTGCTGTTTATGTCTCTGAGAAATGCCTGCATTTAA
```

Nucleotide Sequence Encoding the huIL22-F8 Conjugate (SEQ ID NO: 14)

The below sequence shows (in order) the sequence encoding: (i) huIL22 [underlined], (ii) a 15 amino acid linker [bold]; (iii) the F8 VH domain [italics]; (iv) a 5 amino acid linker [bold and underlined]; (v) the F8 VL domain; and (vi) the stop codon [bold]

```
huIL22 - 15 AA Linker - F8V_H - 5 AA Linker - F8V_L
GCGCCCATCAGCTCCCACTGCAGGCTTGACAAGTCCAACTTCCAGCAGCC

CTATATCACCAACCGCACCTTCATGCTGGCTAAGGAGGCTAGCTTGGCTG

ATAACAACACAGACGTTCGTCTCATTGGGGAGAAACTGTTCCACGGAGTC

AGTATGAGTGAGCGCTGCTATCTGATGAAGCAGGTGCTGAACTTCACCCT

TGAAGAAGTGCTGTTCCCTCAATCTGATAGGTTCCAGCCTTATATGCAGG

AGGTGGTGCCCTTCCTGGCCAGGCTCAGCAACAGGCTAAGCACATGTCAT

ATTGAAGGTGATGACCTGCATATCCAGAGGAATGTGCAAAAGCTGAAGGA

CACAGTGAAAAAGCTTGGAGAGAGTGGAGAGATCAAAGCAATTGGAGAAC

TGGATTTGCTGTTTATGTCTCTGAGAAATGCCTGCATTGGTGGAGGCGGT

TCAGGCGGAGGTGGCTCTGGCGGTGGCGGATCAGAGGTGCAGCTGTTGGA

GTCTGGGGGAGGCTTGGTACAGCCTGGGGGGTCCCTGAGACTCTCCTGTG

CAGCCTCTGGATTCACCTTTAGCCTGTTTACGATGAGCTGGGTCCGCCAG

GCTCCAGGGAAGGGGCTGGAGTGGGTCTCAGCTATTAGTGGTAGTGGTGG

TAGCACATACTACGCAGACTCCGTGAAGGGCCGGTTCACCATCTCCAGAG

ACAATTCCAAGAACACGCTGTATCTGCAAATGAACAGCCTGAGAGCCGAG

GACACGGCCGTATATTACTGTGCGAAAAGTACTCATTTGTATCTTTTTGA
```

```
CTACTGGGGCCAGGGAACCCTGGTCACCGTCTCGAGTGGGCGGTAGCGGA

GGGGAAATTGTGTTGACGCAGTCTCCAGGCACCCTGTCTTTGTCTCCAGG

GGAAAGAGCCACCCTCTCCTGCAGGGCCAGTCAGAGTGTTAGCATGCCGG

TTTTAGCCTGGTACCAGCAGAAACCTGGCCAGGCTCCCAGGCTCCTCATC

TATGGTGCATCCAGCAGGGCCACTGGCATCCCAGACAGGTTCAGTGGCAG

TGGGTCTGGGACAGACTTCACTCTCACCATCAGCAGACTGGAGCCTGAAG

ATTTTGCAGTGTATTACTGTCAGCAGATGCGTGGTCGGCCGCCGACGTTC

GGCCAAGGGACCAAGGTGGAAATCAAA
```

Nucleotide Sequence Encoding the F8-huIL22 conjugate (SEQ ID NO: 15)

The below sequence shows (in order) the sequence encoding: (i) the F8 VH domain [itallics]; (ii) a 5 amino acid linker [bold and underlined]; (iii) the F8 VL domain; (iv) a 15 amino acid linker [bold]; huIL22 [underlined]; and (vi) the stop codon [bold]

```
F8VH - 5 AA Linker - F8VL - 15 AA Linker - huIL22
GAGGTGCAGCTGTTGGAGTCTGGGGGAGGCTTGGTACAGCCTGGGGGGTC

CCTGAGACTCTCCTGTGCAGCCTCTGGATTCACCTTTAGCCTGTTTACGA

TGAGCTGGGTCCGCCAGGCTCCAGGGAAGGGGCTGGAGTGGGTCTCAGCT

ATTAGTGGTAGTGGTGGTAGCACATACTACGCAGACTCCGTGAAGGGCCG

GTTCACCATCTCCAGAGACAATTCCAAGAACACGCTGTATCTGCAAATGA

ACAGCCTGAGAGCCGAGGACACGGCCGTATATTACTGTGCGAAAAGTACT

CATTTGTATCTTTTTGACTACTGGGGCCAGGGAACCCTGGTCACCGTCTC

GAGTGGCGGTAGCGGAGGGGAAATTGTGTTGACGCAGTCTCCAGGCACCC

TGTCTTTGTCTCCAGGGGAAAGAGCCACCCTCTCCTGCAGGGCCAGTCAG

AGTGTTAGCATGCCGTTTTTAGCCTGGTACCAGCAGAAACCTGGCCAGGC

TCCCAGGCTCCTCATCTATGGTGCATCCAGCAGGGCCACTGGCATCCCAG

ACAGGTTCAGTGGCAGTGGGTCTGGGACAGACTTCACTCTCACCATCAGC

AGACTGGAGCCTGAAGATTTTGCAGTGTATTACTGTCAGCAGATGCGTGG

TCGGCCGCCGACGTTCGGCCAAGGGACCAAGGTGGAAATCAAAgGTGGAG

GCGGTTCAGGCGGAGGTGGCTCTGGCGGTGGCGGATCAGCGCCCATCAGC

TCCCACTGCAGGCTTGACAAGTCCAACTTCCAGCAGCCCTATATCACCAA

CCGCACCTTCATGCTGGCTAAGGAGGCTAGCTTGGCTGATAACAACACAG

ACGTTCGTCTCATTGGGGAGAAACTGTTCCACGGAGTCAGTATGAGTGAG

CGCTGCTATCTGATGAAGCAGGTGCTGAACTTCACCCTTGAAGAAGTGCT

GTTCCCTCAATCTGATAGGTTCCAGCCTTATATGCAGGAGGTGGTGCCCT

TCCTGGCCAGGCTCAGCAACAGGCTAAGCACATGTCATATTGAAGGTGAT

GACCTGCATATCCAGAGGAATGTGCAAAAGCTGAAGGACACAGTGAAAAA

GCTTGGAGAGAGTGGAGAGATCAAAGCAATTGGAGAACTGGATTTGCTGT

TTATGTCTCTGAGAAATGCCTGCATT
```

Amino Acid Sequence of the huIL22-F8 Conjugate (SEQ ID NO: 16)

The below sequence shows (in order) the amino acid sequence of: (i) huIL22 [underlined], (ii) a 15 amino acid linker [bold]; (iii) the F8 VH domain [itallics]; (iv) a 5 amino acid linker [bold and underlined]; and (v) the F8 VL domain.

APISSHCRLDKSNFQQPYITNRTFMLAKEASLADNNTDVRLIGEKLFHGV
SMSERCYLMKQVLNFTLEEVLFPQSDRFQPYMQEVVPFLARLSNRLSTCH
IEGDDLHIQRNVQKLKDTVKKLGESGEIKAIGELDLLFMSLRNACIGGGG
SGGGGSGGGGSEVQLLESGGGLVQPGGSLRLSCAASGFTFSLFTMSWVRQ
APGKGLEWVSAISGSGGSTYYADSVKGRFTISRDNSKNTLYLQMNSLRAE
DTAVYYCAKSTHLYLFDYWGQGTLVTVSSGGSGGEIVLTQSPGTLSLSPG
ERATLSCRASQSVSMPFLAWYQQKPGQAPRLLIYGASSRATGIPDRFSGS
GSGTDFTLTISRLEPEDFAVYYCQQMRGRPPTFGQGTKVEIK

Amino Acid Sequence of the F8-huIL22 Conjugate (SEQ ID NO: 17)

The below sequence shows (in order) the amino acid sequence of: (i) the F8 VH domain [itallics]; (ii) a 5 amino acid linker [bold and underlined]; (iii) the F8 VL domain; (iv) a 15 amino acid linker [bold]; and huIL22 [underlined].

*EVQLLESGGGLVQPGGSLRLSCAASGFTFSLFTMSWVRQAPGKGLEWVSA*
*ISGSGGSTYYADSVKGRFTISRDNSKNTLYLQMNSLRAEDTAVYYCAKST*
*HLYLFDYWGQGTLVTVSS*GGSGGEIVLTQSPGTLSLSPGERATLSCRASQ
SVSMPFLAWYQQKPGQAPRLLIYGASSRATGIPDRFSGSGSGTDFTLTIS
RLEPEDFAVYYCQQMRGRPPTFGQGTKVEIKGGGGSGGGGSGGGGSAPIS
SHCRLDKSNFQQPYITNRTFMLAKEASLADNNTDVRLIGEKLFHGVSMSE
RCYLMKQVLNFTLEEVLFPQSDRFQPYMQEVVPFLARLSNRLSTCHIEGD
DLHIQRNVQKLKDTVKKLGESGEIKAIGELDLLFMSLRNACI

Amino acid sequence of mus musculus IL22 (mulL22)
(SEQ ID NO: 18)
LPVNTRCKLEVSNFQQPYIVNRTFMLAKEASLADNNTDVRLIGEKLFRGV
SAKDQCYLMKQVLNFTLEDVLLPQSDRFQPYMQEVVPFLTKLSNQLSSCH
ISGDDQNIQKNVRRLKETVKKLGESGEIKAIGELDLLFMSLRNACV Amino acid sequence of the linker linking mulL22 to the F8 VH domain in the mulL22-F8 conjugate
(SEQ ID NO: 19)
GGGGSGGGGSGGGGS Amino acid sequence of the linker linking mulL22 to the F8 VL domain in the F8-mulL22 conjugate
(SEQ ID NO: 20)
GGGGSGGGGSGGGGS Nucleotide Sequence Encoding the MuIL22-F8 Conjugate (SEQ ID NO: 21)

muIL22-15AA Linker-F8$V_H$-5AA Linker-F8$V_L$

The below sequence shows (in order) the sequence encoding: (i) muIL22 [underlined], (ii) a 15 amino acid linker [bold]; (iii) the F8 VH domain [itallics]; (iv) a 5 amino acid linker [bold and underlined]; (v) the F8 VL domain; and (vi) the stop codon [bold]

CTGCCCGTCAACACCCGGTGCAAGCTTGAGGTGTCCAACTTCCAGCAGCC
GTACATCGTCAACCGCACCTTTATGCTGGCCAAGGAGGCCAGCCTTGCAG
ATAACAACACAGATGTCCGGCTCATCGGGGAGAAACTGTTCCGAGGAGTC

-continued

AGTGCTAAGGATCAGTGCTACCTGATGAAGCAGGTGCTCAACTTCACCCT
GGAAGACGTTCTGCTCCCCCAGTCAGACAGGTTCCAGCCCTACATGCAGG
AGGTGGTGCCTTTCCTGACCAAACTCAGCAATCAGCTCAGCTCCTGTCAC
ATCAGCGGTGACGACCAGAACATCCAGAAGAATGTCAGAAGGCTGAAGGA
GACAGTGAAAAAGCTTGGAGAGAGTGGAGAGATCAAGGCGATTGGGGAAC
TGGACCTGCTGTTTATGTCTCTGAGAAATGCTTGCGTCGGTGGAGGCGGT
TCAGGCGGAGGTGGCTCTGGCGGTGGCGGATCA*GAGGTGCAGCTGTTGGA*
*GTCTGGGGGAGGCTTGGTACAGCCTGGGGGGTCCCTGAGACTCTCCTGTG*
*CAGCCTCTGGATTCACCTTTAGCCTGTTTACGATGAGCTGGGTCCGCCAG*
*GCTCCAGGGAAGGGGCTGGAGTGGGTCTCAGCTATTAGTGGTAGTGGTGG*
*TAGCACATACTACGCAGACTCCGTGAAGGGCCGGTTCACCATCTCCAGAG*
*ACAATTCCAAGAACACGCTGTATCTGCAAATGAACAGCCTGAGAGCCGAG*
*GACACGGCCGTATATTACTGTGCGAAAAGTACTCATTTGTATCTTTTTGA*
*CTACTGGGGCCAGGGAACCCTGGTCACCGTCTCGAGT*GGCGGTAGCGGAG
GGGAAATTGTGTTGACGCAGTCTCCAGGCACCCTGTCTTTGTCTCCAGGG
GAAAGAGCCACCCTCTCCTGCAGGGCCAGTCAGAGTGTTAGCATGCCGTT
TTTAGCCTGGTACCAGCAGAAACCTGGCCAGGCTCCCAGGCTCCTCATCT
ATGGTGCATCCAGCAGGGCCACTGGCATCCCAGACAGGTTCAGTGGCAGT
GGGTCTGGGACAGACTTCACTCTCACCATCAGCAGACTGGAGCCTGAAGA
TTTTGCAGTGTATTACTGTCAGCAGATGCGTGGTCGGCCGCCGACGTTCG
GCCAAGGGACCAAGGTGGAAATCAAA

Nucleotide Sequence Encoding the F8-muIL22 Conjugate (SEQ ID NO: 22)

F8$V_H$-5AA Linker-F8$V_L$-15AA Linker-muIL22

The below sequence shows (in order) the sequence encoding: (i) the F8 VH domain [itallics]; (ii) a 5 amino acid linker [bold and underlined]; (iii) the F8 VL domain; (iv) a 15 amino acid linker [bold]; muIL22 [underlined]; and (vi) the stop codon [bold]

*GAGGTGCAGCTGTTGGAGTCTGGGGGAGGCTTGGTACAGCCTGGGGGGTC*
*CCTGAGACTCTCCTGTGCAGCCTCTGGATTCACCTTTAGCCTGTTTACGA*
*TGAGCTGGGTCCGCCAGGCTCCAGGGAAGGGGCTGGAGTGGGTCTCAGCT*
*ATTAGTGGTAGTGGTGGTAGCACATACTACGCAGACTCCGTGAAGGGCCG*
*GTTCACCATCTCCAGAGACAATTCCAAGAACACGCTGTATCTGCAAATGA*
*ACAGCCTGAGAGCCGAGGACACGGCCGTATATTACTGTGCGAAAAGTACT*
*CATTTGTATCTTTTTGACTACTGGGGCCAGGGAACCCTGGTCACCGTCTC*
*GAGT*GGCGGTAGCGGAGGGGAAATTGTGTTGACGCAGTCTCCAGGCACCC
TGTCTTTGTCTCCAGGGGAAAGAGCCACCCTCTCCTGCAGGGCCAGTCAG
AGTGTTAGCATGCCGTTTTTAGCCTGGTACCAGCAGAAACCTGGCCAGGC
TCCCAGGCTCCTCATCTATGGTGCATCCAGCAGGGCCACTGGCATCCCAG
ACAGGTTCAGTGGCAGTGGGTCTGGGACAGACTTCACTCTCACCATCAGC
AGACTGGAGCCTGAAGATTTTGCAGTGTATTACTGTCAGCAGATGCGTGG

```
TCGGCCGCCGACGTTCGGCCAAGGGACCAAGGTGGAAATCAAAGGTGGAG

GCGGTTCAGGCGGAGGTGGCTCTGGCGGTGGCGGATCACTGCCCGTCAAC

ACCCGGTGCAAGCTTGAGGTGTCCAACTTCCAGCAGCCGTACATCGTCAA

CCGCACCTTTATGCTGGCCAAGGAGGCCAGCCTTGCAGATAACAACACAG

ATGTCCGGCTCATCGGGGAGAAACTGTTCCGAGGAGTCAGTGCTAAGGAT

CAGTGCTACCTGATGAAGCAGGTGCTCAACTTCACCCTGGAAGACGTTCT

GCTCCCCAGTCAGACAGGTTCCAGCCCTACATGCAGGAGGTGGTGCCTT

TCCTGACCAAACTCAGCAATCAGCTCAGCTCCTGTCACATCAGCGGTGAC

GACCAGAACATCCAGAAGAATGTCAGAAGGCTGAAGGAGACAGTGAAAAA

GCTTGGAGAGAGTGGAGAGATCAAGGCGATTGGGGAACTGGACCTGCTGT

TTATGTCTCTGAGAAATGCTTGCGTC
```

Amino Acid Sequence of the muIL22-F8 Conjugate (SEQ ID NO: 23)

The below sequence shows (in order) the amino acid sequence of: (i) muIL22 [underlined], (ii) a 15 amino acid linker [bold]; (iii) the F8 VH domain [itallics]; (iv) a 5 amino acid linker [bold and underlined]; and (v) the F8 VL domain.

LPVNTRCKLEVSNFQQPYIVNRTFMLAKEASLADNNTDVRLIGEKLFRGV

SAKDQCYLMKQVLNFTLEDVLLPQSDRFQPYMQEVVPFLTKLSNQLSSCH

ISGDDQNIQKNVRRLKETVKKLGESGEIKAIGELDLLFMSLRNACVGGGG

SGGGGSGGGGSEVQLLESGGGLVQPGGSLRLSCAASGFTFSLFTMSWVRQ

APGKGLEWVSAISGSGGSTYYADSVKGRFTISRDNSKNTLYLQMNSLRAE

DTAVYYCAKSTHLYLFDYWGQGTLVTVSSGSGGGEIVLTQSPGTLSLSPG

ERATLSCRASQSVSMPFLAWYQQKPGQAPRLLIYGASSRATGIPDRFSGS

GSGTDFTLTISRLEPEDFAVYYCQQMRGRPPTFGQGTKVEIK

Amino Acid Sequence of the F8-muIL22 Conjugate (SEQ ID NO: 24)

The below sequence shows (in order) the amino acid sequence of: (i) the F8 VH domain [itallics]; (ii) a 5 amino acid linker [bold and underlined]; (iii) the F8 VL domain; (iv) a 15 amino acid linker [bold]; and muIL22 [underlined].

EVQLLESGGGLVQPGGSLRLSCAASGFTFSLFTMSWVRQAPGKGLEWVS

AISGSGGSTYYADSVKGRFTISRDNSKNTLYLQMNSLRAEDTAVYYCAKS

THLYLFDYWGQGTLVTVSSGSGGGEIVLTQSPGTLSLSPGERATLSCRAS

QSVSMPFLAWYQQKPGQAPRLLIYGASSRATGIPDRFSGSGSGTDFTLTI

SRLEPEDFAVYYCQQMRGRPPTFGQGTKVEIKGGGGSGGGGSGGGGSLPV

NTRCKLEVSNFQQPYIVNRTFMLAKEASLADNNTDVRLIGEKLFRGVSAK

DQCYLMKQVLNFTLEDVLLPQSDRFQPYMQEVVPFLTKLSNQLSSCHISG

DDQNIQKNVRRLKETVKKLGESGEIKAIGELDLLFMSLRNACV

Amino acid sequence of L19 CDR's (SEQ ID NO: 25)
L19 CDR1 VH - Ser Phe Ser Met Ser (SEQ ID NO: 26)
L19 CDR2 VH - Ser Ile Ser Gly Ser Ser Gly Thr Thr Tyr Tyr Ala Asp Ser Val Lys (SEQ ID NO: 27)
L19 CDR3 VH - Pro Phe Pro Tyr Phe Asp Tyr (SEQ ID NO: 28)
L19 CDR1 VL - Arg Ala Ser Gln Ser Val Ser Ser Ser Phe Leu Ala (SEQ ID NO: 29)
L19 CDR2 VL - Tyr Ala Ser Ser Arg Ala Thr (SEQ ID NO: 30)
L19 CDR3 VL - Gln Gln Thr Gly Arg Ile Pro Pro Thr Amino acid sequence of L19 VH domain (SEQ ID NO: 31)
Glu Val Gln Leu Leu Glu Ser Gly Gly Gly Leu Val Gln Pro Gly Gly Ser Leu Arg Leu Ser Cys Ala Ala Ser Gly Phe Thr Phe Ser Ser Phe Ser Met Ser Trp Val Arg Gln Ala Pro Gly Lys Gly Leu Glu Trp Val Ser Ser Ile Ser Gly Ser Ser Gly Thr Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Lys Pro Phe Pro Tyr Phe Asp Tyr Trp Gly Gln Gly Thr Leu Val Thr Val Ser Ser Amino acid sequence of L19 VL domain (SEQ ID NO: 32)
Glu Ile Val Leu Thr Gln Ser Pro Gly Thr Leu Ser Leu Ser Pro Gly Glu Arg Ala Thr Leu Ser Cys Arg Ala Ser Gln Ser Val Ser Ser Ser Phe Leu Ala Trp Tyr Gln Gln Lys Pro Gly Gln Ala Pro Arg Leu Leu Ile Tyr Tyr Ala Ser Ser Arg Ala Thr Gly Ile Pro Asp Arg Phe Ser Gly Ser Gly Ser Gly Thr Asp Phe Thr Leu Thr Ile Ser Arg Leu Glu Pro Glu Asp Phe Ala Val Tyr Tyr Cys Gln Gln Thr Gly Arg Ile Pro Pro Thr Phe Gly Gln Gly Thr Lys Val Glu Ile Lys Amino acid sequence of L19 diabody (SEQ ID NO: 33)
The VH and VL domain linker sequence is shown underlined Glu Val Gln Leu Leu Glu Ser Gly Gly Gly Leu Val Gln Pro Gly Gly Ser Leu Arg Leu Ser Cys Ala Ala Ser Gly Phe Thr Phe Ser Ser Phe Ser Met Ser Trp Val Arg Gln Ala Pro Gly Lys Gly Leu Glu Trp Val Ser Ser Ile Ser Gly Ser Ser Gly Thr Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys -continued

```
Ala Lys Pro Phe Pro Tyr Phe Asp Tyr Trp Gly Gln

Gly Thr Leu Val Thr Val Ser Ser Gly Gly Ser Gly

Gly Glu Ile Val Leu Thr Gln Ser Pro Gly Thr Leu

Ser Leu Ser Pro Gly Glu Arg Ala Thr Leu Ser Cys

Arg Ala Ser Gln Ser Val Ser Ser Ser Phe Leu Ala

Trp Tyr Gln Gln Lys Pro Gly Gln Ala Pro Arg Leu

Leu Ile Tyr Tyr Ala Ser Ser Arg Ala Thr Gly Ile

Pro Asp Arg Phe Ser Gly Ser Gly Ser Gly Thr Asp

Phe Thr Leu Thr Ile Ser Arg Leu Glu Pro Glu Asp

Phe Ala Val Tyr Tyr Cys Gln Gln Thr Gly Arg Ile

Pro Pro Thr Phe Gly Gln Gly Thr Lys Val Glu Ile

Lys
```

Amino acid sequence of F16 CDR's (SEQ ID NO: 34)
F16 CDR1 VH - RYGMS (SEQ ID NO: 35)
F16 CDR2 VH - AISGSGGSTYYADSVKG (SEQ ID NO: 36)
F16 CDR3 VH - AHNAFDY (SEQ ID NO: 37)
F16 CDR1 VL - QGDSLRSYYAS (SEQ ID NO: 38)
F16 CDR2 VL - GKNNRPS (SEQ ID NO: 39)
F16 CDR3 VL - NSSVYTMPPVV Amino acid sequence F16 VH domain (SEQ ID NO: 40)
EVQLLESGGGLVQPGGSLRLSCAASGFTFSRYGMSWVRQAPGKGLEWVSA

ISGSGGSTYYADSVKGRFTISRDNSKNTLYLQMNSLRAEDTAVYYCAKAH

NAFDYVVGQGTLVTVSR

Amino acid sequence F16 VL domain (SEQ ID NO: 41)
SSELTQDPAVSVALGQTVRITCQGDSLRSYYASWYQQKPGQAPVLVIYGK

NNRPSGIPDRFSGSSSGNTASLTITGAQAEDEADYYCNSSVYTMPPVVFG

GGTKLTVL

Amino acid sequence of the F16 diabody (SEQ ID NO: 42)
The VH and VL domain linker sequence is shown
underlined
EVQLLESGGGLVQPGGSLRLSCAASGFTFSRYGMSWVRQAPGKGLEWVSA

ISGSGGSTYYADSVKGRFTISRDNSKNTLYLQMNSLRAEDTAVYYCAKAH

NAFDYVVGQGTLVTVSR<u>GGSGGS</u>SELTQDPAVSVALGQTVRITCQGDSLR

SYYASWYQQKPGQAPVLVIYGKNNRPSGIPDRFSGSSSGNTASLTITGAQ

AEDEADYYCNSSVYTMPPVVFGGGTKLTVL

VH and VL domain linker sequence in an scFv
molecule (SEQ ID NO: 43)
GGGSGGGSGG

REFERENCES

All documents mentioned in this specification are incorporated herein by reference in their entirety.

Li, L. J., C. Gong, M. H. Zhao and B. S. Feng (2014). "Role of interleukin-22 in inflammatory bowel disease." *World J Gastroenterol* 20(48): 18177-18188.

Muller, N., M. Derouazi, F. Van Tilborgh, S. Wulhfard, D. L. Hacker, M. Jordan and F. M. Wurm (2007). "Scalable transient gene expression in Chinese hamster ovary cells in instrumented and non-instrumented cultivation systems." *Biotechnol Lett* 29(5): 703-711.

Murphy, K. (2012). *Janeway's Immunobiology*, Garland Science.

Savage, P., So, A., Spooner, R. A. & Epenetos, A. A. A recombinant single chain antibody interleukin-2 fusion protein. *Br J Cancer* 67, 304-310 (1993).

Schrama, D., Reisfeld, R. A. & Becker, J. C. Antibody targeted drugs as cancer therapeutics. *Nat Rev Drug Discov* 5, 147-159 (2006).

Neri, D. & Bicknell, R. Tumour vascular targeting. *Nat Rev Cancer* 5, 436-446 (2005).

Dela Cruz, J. S., Huang, T. H., Penichet, M. L. & Morrison, S. L. Antibody-cytokine fusion proteins: innovative weapons in the war against cancer. *Clin Exp Med* 4, 57-64 (2004).

Reisfeld, R. A., Becker, J. C. & Gillies, S. D. Immunocytokines: a new approach to immunotherapy of melanoma. *Melanoma Res* 7 Suppl 2, S99-106 (1997).

Kontermann R E. Antibody-cytokine fusion proteins. Arch Biochem Biophys. 2012; 526:194-205.

Borsi L, Balza E, Carnemolla B, Sassi F, Castellani P, Berndt A, et al. Selective targeted delivery of TNFalpha to tumor blood vessels. Blood. 2003; 102:4384-92.

Carnemolla B, Borsi L, Balza E, Castellani P, Meazza R, Berndt A, et al. Enhancement of the antitumor properties of interleukin-2 by its targeted delivery to the tumor blood vessel extracellular matrix. Blood. 2002; 99:1659-65.

Frey K, Schliemann C, Schwager K, Giavazzi R, Johannsen M, Neri D. The immunocytokine F8-IL2 improves the therapeutic performance of sunitinib in a mouse model of renal cell carcinoma. J Urol. 2010; 184:2540-8.

Kaspar M, Trachsel E, Neri D. The antibody-mediated targeted delivery of interleukin-15 and GM-CSF to the tumor neovasculature inhibits tumor growth and metastasis. Cancer Res. 2007; 67:4940-8

Pasche N, Frey K, Neri D. The targeted delivery of IL17 to the mouse tumor neo-vasculature enhances angiogenesis but does not reduce tumor growth rate. Angiogenesis. 2012; 15:165-9.

Pasche N, Neri D. Immunocytokines: a novel class of potent armed antibodies. Drug Discov Today. 2012; 17:583-90.

Schwager et al., Preclinical characterization of DEKAVIL (F8-IL10), a novel clinical-stage immunocytokine which inhibits the progression of collagen-induced arthritis. Arthritis Research & Therapy 2009, 11(5):R142.

Schwager K, Bootz F, Imesch P, Kaspar M, Trachsel E, Neri D. The antibody-mediated targeted delivery of interleukin-10 inhibits endometriosis in a syngeneic mouse model. Hum Reprod. 2011; 26:2344-52.

Schwager K, Kaspar M, Bootz F, Marcolongo R, Paresce E, Neri D, et al. Preclinical characterization of DEKAVIL (F8-IL10), a novel clinical-stage immunocytokine which inhibits the progression of collagen-induced arthritis. Arthritis Res Ther. 2009; 11:R142.

Schwager K, Villa A, Rosli C, Neri D, Rosli-Khabas M, Moser G. A comparative immunofluorescence analysis of three clinical-stage antibodies in head and neck cancer. Head Neck Oncol. 2011; 3:25.

Brack S S, Silacci M, Birchler M, Neri D. Tumor-targeting properties of novel antibodies specific to the large isoform of tenascin-C. Clin Cancer Res. 2006; 12:3200-8.

Pedretti M, Soltermann A, Arni S, Weder W, Neri D, Hillinger S. Comparative immunohistochemistry of L19 and F16 in non-small cell lung cancer and mesothelioma: two human antibodies investigated in clinical trials in patients with cancer. Lung Cancer. 2009; 64:28-33.

Schliemann C, Palumbo A, Zuberbuhler K, Villa A, Kaspar M, Trachsel E, et al. Complete eradication of human B-cell lymphoma xenografts using rituximab in combination with the immunocytokine L19-IL2. Blood. 2009; 113:2275-83.

Schliemann C, Wiedmer A, Pedretti M, Szczepanowski M, Klapper W, Neri D. Three clinical-stage tumor targeting antibodies reveal differential expression of oncofetal fibronectin and tenascin-C isoforms in human lymphoma. Leuk Res. 2009; 33:1718-22.

Schliemann C, Palumbo A, Zuberbuhler K, Villa A, Kaspar M, Trachsel E, et al. Complete eradication of human B-cell lymphoma xenografts using rituximab in combination with the immunocytokine L19-IL2. Blood. 2009; 113:2275-83.

Villa A, Trachsel E, Kaspar M, Schliemann C, Sommavilla R, Rybak J N, et al. A high-affinity human monoclonal antibody specific to the alternatively spliced EDA domain of fibronectin efficiently targets tumor neo-vasculature in vivo. Int J Cancer. 2008; 122:2405-13.

Viti F, Tarli L, Giovannoni L, Zardi L, Neri D. Increased binding affinity and valence of recombinant antibody fragments lead to improved targeting of tumoral angiogenesis. Cancer Res. 1999; 59:347-52.

Eigentler T K, Weide B, de Braud F, Spitaleri G, Romanini A, Pflugfelder A, et al. A dose-escalation and signal-generating study of the immunocytokine L19-IL2 in combination with dacarbazine for the therapy of patients with metastatic melanoma. Clin Cancer Res. 2011; 17:7732-42.

Papadia F, Basso V, Patuzzo R, Maurichi A, Di Florio A, Zardi L, et al. Isolated limb perfusion with the tumor-targeting human monoclonal antibody-cytokine fusion protein L19-TNF plus melphalan and mild hyperthermia in patients with locally advanced extremity melanoma. J Surg Oncol. 2012.

Smith et al. IL-22 Regulates Iron Availability In Vivo through the Induction of Hepcidin. *J Immunol* 2013; 191:1845-1855.

SEQUENCE LISTING

```
<160> NUMBER OF SEQ ID NOS: 43

<210> SEQ ID NO 1
<211> LENGTH: 3
<212> TYPE: PRT
<213> ORGANISM: Artificial Sequence
<220> FEATURE:
<223> OTHER INFORMATION: F8 CDR1 VH

<400> SEQUENCE: 1

Leu Phe Thr
1

<210> SEQ ID NO 2
<211> LENGTH: 6
<212> TYPE: PRT
<213> ORGANISM: Artificial Sequence
<220> FEATURE:
<223> OTHER INFORMATION: F8 CDR2 VH

<400> SEQUENCE: 2

Ser Gly Ser Gly Gly Ser
1               5

<210> SEQ ID NO 3
<211> LENGTH: 6
<212> TYPE: PRT
<213> ORGANISM: Artificial Sequence
<220> FEATURE:
<223> OTHER INFORMATION: F8 CDR3 VH

<400> SEQUENCE: 3

Ser Thr His Leu Tyr Leu
1               5

<210> SEQ ID NO 4
<211> LENGTH: 3
<212> TYPE: PRT
<213> ORGANISM: Artificial Sequence
<220> FEATURE:
```

-continued

<223> OTHER INFORMATION: F8 CDR1 VL

<400> SEQUENCE: 4

Met Pro Phe
1

<210> SEQ ID NO 5
<211> LENGTH: 7
<212> TYPE: PRT
<213> ORGANISM: Artificial Sequence
<220> FEATURE:
<223> OTHER INFORMATION: F8 CDR2 VL

<400> SEQUENCE: 5

Gly Ala Ser Ser Arg Ala Thr
1               5

<210> SEQ ID NO 6
<211> LENGTH: 6
<212> TYPE: PRT
<213> ORGANISM: Artificial Sequence
<220> FEATURE:
<223> OTHER INFORMATION: F8 CDR3 VL

<400> SEQUENCE: 6

Met Arg Gly Arg Pro Pro
1               5

<210> SEQ ID NO 7
<211> LENGTH: 118
<212> TYPE: PRT
<213> ORGANISM: Artificial Sequence
<220> FEATURE:
<223> OTHER INFORMATION: F8 VH domain

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
                20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: F8 VL domain

<400> SEQUENCE: 8

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Met Pro
                20                  25                  30

Phe Leu Ala Trp Tyr Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Met Arg Gly Arg Pro
                85                  90                  95

Pro Thr Phe Gly Gln Gly Thr Lys Val Glu Ile Lys
            100                 105
```

<210> SEQ ID NO 9
<211> LENGTH: 5
<212> TYPE: PRT
<213> ORGANISM: Artificial Sequence
<220> FEATURE:
<223> OTHER INFORMATION: Linker linking F8 VH domain to the F8 VL domain
      in the F8 diabody

<400> SEQUENCE: 9

```
Gly Gly Ser Gly Gly
 1               5
```

<210> SEQ ID NO 10
<211> LENGTH: 231
<212> TYPE: PRT
<213> ORGANISM: Artificial Sequence
<220> FEATURE:
<223> OTHER INFORMATION: F8 diabody

<400> SEQUENCE: 10

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Phe
                20                  25                  30

Thr Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Thr His Leu Tyr Leu Phe Asp Tyr Trp Gly Gln Gly Thr
            100                 105                 110

Leu Val Thr Val Ser Ser Gly Gly Ser Gly Gly Glu Ile Val Leu Thr
            115                 120                 125

Gln Ser Pro Gly Thr Leu Ser Leu Ser Pro Gly Glu Arg Ala Thr Leu
            130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
            180                 185                 190
```

Thr Asp Phe Thr Leu Thr Ile Ser Arg Leu Glu Pro Glu Asp Phe Ala
            195                 200                 205

Val Tyr Tyr Cys Gln Gln Met Arg Gly Arg Pro Pro Thr Phe Gly Gln
    210                 215                 220

Gly Thr Lys Val Glu Ile Lys
225                 230

<210> SEQ ID NO 11
<211> LENGTH: 146
<212> TYPE: PRT
<213> ORGANISM: Homo sapiens

<400> SEQUENCE: 11

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 12
<211> LENGTH: 15
<212> TYPE: PRT
<213> ORGANISM: Artificial Sequence
<220> FEATURE:
<223> OTHER INFORMATION: Linker linking huIL22 to the F8 VH domain in
      the huIL22-F8 conjuage and huIL22 to the F8 VL domain in the
      F8-huIL22 conjugate

<400> SEQUENCE: 12

Gly Gly Gly Gly Ser Gly Gly Gly Ser Gly Gly Gly Gly Ser
1               5                   10                  15

<210> SEQ ID NO 13
<211> LENGTH: 441
<212> TYPE: DNA
<213> ORGANISM: Homo sapiens

<400> SEQUENCE: 13
gcgcccatca gctcccactg caggcttgac aagtccaact tccagcagcc ctatatcacc     60
aaccgcacct tcatgctggc taaggaggct agcttggctg ataacaacac agacgttcgt    120
ctcattgggg agaaactgtt ccacggagtc agtatgagtg agcgctgcta tctgatgaag    180
caggtgctga acttcaccct tgaagaagtg ctgttccctc aatctgatag gttccagcct    240
tatatgcagg aggtggtgcc cttcctggcc aggctcagca acaggctaag cacatgtcat    300

```
attgaaggtg atgacctgca tatccagagg aatgtgcaaa agctgaagga cacagtgaaa    360
aagcttggag agagtggaga gatcaaagca attggagaac tggatttgct gtttatgtct    420
ctgagaaatg cctgcattta a                                              441
```

<210> SEQ ID NO 14
<211> LENGTH: 1176
<212> TYPE: DNA
<213> ORGANISM: Artificial Sequence
<220> FEATURE:
<223> OTHER INFORMATION: huIL22-F8 conjugate
<400> SEQUENCE: 14

```
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag  cacatgtcat     300 attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattgg tggaggcggt tcaggcggag gtggctctgg cggtggcgga     480
tcagaggtgc agctgttgga gtctggggga ggcttggtac agcctggggg gtccctgaga     540
ctctcctgtg cagcctctgg attcaccttt agcctgttta cgatgagctg ggtccgccag     600
gctccaggga aggggctgga gtgggtctca gctattagtg gtagtggtgg tagcacatac     660
tacgcagact ccgtgaaggg ccggttcacc atctccagag acaattccaa gaacacgctg     720
tatctgcaaa tgaacagcct gagagccgag gacacggccg tatattactg tgcgaaaagt     780
actcatttgt atcttttga  ctactggggc cagggaaccc tggtcaccgt ctcgagtggc     840
ggtagcggag gggaaattgt gttgacgcag tctccaggca ccctgtcttt gtctccaggg     900
gaaagagcca ccctctcctg cagggccagt cagagtgtta gcatgccgtt tttagcctgg     960
taccagcaga aacctggcca ggctcccagg ctcctcatct atggtgcatc cagcagggcc    1020
actggcatcc cagacaggtt cagtggcagt gggtctggga cagacttcac tctcaccatc    1080
agcagactgg agcctgaaga ttttgcagtg tattactgtc agcagatgcg tggtcggccg    1140
ccgacgttcg gccaagggac caaggtggaa atcaaa                              1176
```

<210> SEQ ID NO 15
<211> LENGTH: 1176
<212> TYPE: DNA
<213> ORGANISM: Artificial Sequence
<220> FEATURE:
<223> OTHER INFORMATION: F8-HuIL22 conjugate
<400> SEQUENCE: 15

```
gaggtgcagc tgttggagtc tgggggaggc ttggtacagc ctggggggtc cctgagactc      60
tcctgtgcag cctctggatt cacctttagc ctgtttacga tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagtact     300
catttgtatc ttttgactac tggggccag  ggaaccctgg tcaccgtctc gagtggcggt     360
```

```
agcggagggg aaattgtgtt gacgcagtct ccaggcaccc tgtctttgtc tccaggggaa    420
agagccaccc tctcctgcag ggccagtcag agtgttagca tgccgttttt agcctggtac    480
cagcagaaac ctggccaggc tcccaggctc ctcatctatg gtgcatccag cagggccact    540
ggcatcccag acaggttcag tggcagtggg tctgggacag acttcactct caccatcagc    600
agactggagc ctgaagattt tgcagtgtat tactgtcagc agatgcgtgg tcggccgccg    660
acgttcggcc aagggaccaa ggtggaaatc aaaggtggag cggttcagg cggaggtggc    720
tctggcggtg gcggatcagc gcccatcagc tcccactgca ggcttgacaa gtccaacttc    780
cagcagccct atatcaccaa ccgcaccttc atgctggcta aggaggctag cttggctgat    840
aacaacacag acgttcgtct cattggggag aaactgttcc acggagtcag tatgagtgag    900
cgctgctatc tgatgaagca ggtgctgaac ttcacccttg aagaagtgct gttccctcaa    960
tctgataggt tccagcctta tatgcaggag gtggtgccct tcctggccag gctcagcaac   1020
aggctaagca catgtcatat tgaaggtgat gacctgcata tccagaggaa tgtgcaaaag   1080
ctgaaggaca cagtgaaaaa gcttggagag agtggagaga tcaaagcaat ggagaactg    1140
gatttgctgt ttatgtctct gagaaatgcc tgcatt                             1176

<210> SEQ ID NO 16
<211> LENGTH: 392
<212> TYPE: PRT
<213> ORGANISM: Artificial Sequence
<220> FEATURE:
<223> OTHER INFORMATION: huIL22-F8 conjugate

<400> SEQUENCE: 16

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Gly Gly Gly Gly Ser Gly Gly Gly Gly Ser Gly Gly Gly Gly
145                 150                 155                 160

Ser Glu Val Gln Leu Leu Glu Ser Gly Gly Gly Leu Val Gln Pro Gly
                165                 170                 175

Gly Ser Leu Arg Leu Ser Cys Ala Ala Ser Gly Phe Thr Phe Ser Leu
            180                 185                 190

Phe Thr Met Ser Trp Val Arg Gln Ala Pro Gly Lys Gly Leu Glu Trp
        195                 200                 205

Val Ser Ala Ile Ser Gly Ser Gly Gly Ser Thr Tyr Tyr Ala Asp Ser
    210                 215                 220
```

```
Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
            245                 250                 255

Cys Ala Lys Ser Thr His Leu Tyr Leu Phe Asp Tyr Trp Gly Gln Gly
            260                 265                 270

Thr Leu Val Thr Val Ser Ser Gly Gly Ser Gly Gly Glu Ile Val Leu
            275                 280                 285

Thr Gln Ser Pro Gly Thr Leu Ser Leu Ser Pro Gly Glu Arg Ala Thr
290                 295                 300

Leu Ser Cys Arg Ala Ser Gln Ser Val Ser Met Pro Phe Leu Ala Trp
305                 310                 315                 320

Tyr Gln Gln Lys Pro Gly Gln Ala Pro Arg Leu Leu Ile Tyr Gly Ala
            325                 330                 335

Ser Ser Arg Ala Thr Gly Ile Pro Asp Arg Phe Ser Gly Ser Gly Ser
            340                 345                 350

Gly Thr Asp Phe Thr Leu Thr Ile Ser Arg Leu Glu Pro Glu Asp Phe
            355                 360                 365

Ala Val Tyr Tyr Cys Gln Gln Met Arg Gly Arg Pro Pro Thr Phe Gly
            370                 375                 380

Gln Gly Thr Lys Val Glu Ile Lys
385                 390

<210> SEQ ID NO 17
<211> LENGTH: 392
<212> TYPE: PRT
<213> ORGANISM: Artificial Sequence
<220> FEATURE:
<223> OTHER INFORMATION: F8-huIL22 conjugate

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Thr His Leu Tyr Leu Phe Asp Tyr Trp Gly Gln Gly Thr
            100                 105                 110

Leu Val Thr Val Ser Ser Gly Gly Ser Gly Gly Glu Ile Val Leu Thr
            115                 120                 125

Gln Ser Pro Gly Thr Leu Ser Leu Ser Pro Gly Glu Arg Ala Thr Leu
130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
            165                 170                 175

Ser Arg Ala Thr Gly Ile Pro Asp Arg Phe Ser Gly Ser Gly Ser Gly
            180                 185                 190
```

```
Thr Asp Phe Thr Leu Thr Ile Ser Arg Leu Glu Pro Glu Asp Phe Ala
        195                 200                 205
Val Tyr Tyr Cys Gln Gln Met Arg Gly Arg Pro Pro Thr Phe Gly Gln
    210                 215                 220
Gly Thr Lys Val Glu Ile Lys Gly Gly Gly Ser Gly Gly Gly Gly
225                 230                 235                 240
Ser Gly Gly Gly Ser Ala Pro Ile Ser Ser His Cys Arg Leu Asp
                245                 250                 255
Lys Ser Asn Phe Gln Gln Pro Tyr Ile Thr Asn Arg Thr Phe Met Leu
            260                 265                 270
Ala Lys Glu Ala Ser Leu Ala Asp Asn Asn Thr Asp Val Arg Leu Ile
        275                 280                 285
Gly Glu Lys Leu Phe His Gly Val Ser Met Ser Glu Arg Cys Tyr Leu
    290                 295                 300
Met Lys Gln Val Leu Asn Phe Thr Leu Glu Glu Val Leu Phe Pro Gln
305                 310                 315                 320
Ser Asp Arg Phe Gln Pro Tyr Met Gln Glu Val Val Pro Phe Leu Ala
                325                 330                 335
Arg Leu Ser Asn Arg Leu Ser Thr Cys His Ile Glu Gly Asp Asp Leu
            340                 345                 350
His Ile Gln Arg Asn Val Gln Lys Leu Lys Asp Thr Val Lys Lys Leu
        355                 360                 365
Gly Glu Ser Gly Glu Ile Lys Ala Ile Gly Glu Leu Asp Leu Leu Phe
    370                 375                 380
Met Ser Leu Arg Asn Ala Cys Ile
385                 390

<210> SEQ ID NO 18
<211> LENGTH: 146
<212> TYPE: PRT
<213> ORGANISM: Mus musculus

<400> SEQUENCE: 18

Leu Pro Val Asn Thr Arg Cys Lys Leu Glu Val Ser Asn Phe Gln Gln
1               5                   10                  15
Pro Tyr Ile Val Asn Arg Thr Phe Met Leu Ala Lys Glu Ala Ser Leu
            20                  25                  30
Ala Asp Asn Asn Thr Asp Val Arg Leu Ile Gly Glu Lys Leu Phe Arg
        35                  40                  45
Gly Val Ser Ala Lys Asp Gln Cys Tyr Leu Met Lys Gln Val Leu Asn
    50                  55                  60
Phe Thr Leu Glu Asp Val Leu Leu Pro Gln Ser Asp Arg Phe Gln Pro
65                  70                  75                  80
Tyr Met Gln Glu Val Val Pro Phe Leu Thr Lys Leu Ser Asn Gln Leu
                85                  90                  95
Ser Ser Cys His Ile Ser Gly Asp Asp Gln Asn Ile Gln Lys Asn Val
            100                 105                 110
Arg Arg Leu Lys Glu Thr Val Lys Lys Leu Gly Glu Ser Gly Glu Ile
        115                 120                 125
Lys Ala Ile Gly Glu Leu Asp Leu Leu Phe Met Ser Leu Arg Asn Ala
    130                 135                 140
Cys Val
145
```

-continued

<210> SEQ ID NO 19
<211> LENGTH: 15
<212> TYPE: PRT
<213> ORGANISM: Artificial Sequence
<220> FEATURE:
<223> OTHER INFORMATION: Linker linking muIL22 to the F8 VH domain in
      the MuIL22-F8 conjugate

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Linker linking muIL22 to the F8 VL somain in
      the F8-muIL22 conjugate

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 1176
<212> TYPE: DNA
<213> ORGANISM: Artificial Sequence
<220> FEATURE:
<223> OTHER INFORMATION: Sequence encoding the muIL22-F8 conjugate

<400> SEQUENCE: 21
ctgcccgtca acacccggtg caagcttgag gtgtccaact tccagcagcc gtacatcgtc      60
aaccgcacct ttatgctggc caaggaggcc agccttgcag ataacaacac agatgtccgg     120
ctcatcgggg agaaactgtt ccgaggagtc agtgctaagg atcagtgcta cctgatgaag     180
caggtgctca acttcaccct ggaagacgtt ctgctccccc agtcagacag gttccagccc     240
tacatgcagg aggtggtgcc tttcctgacc aaactcagca atcagctcag ctcctgtcac     300
atcagcggtg acgaccagaa catccagaag aatgtcagaa ggctgaagga cacagtgaaa     360
aagcttggag agagtggaga gatcaaggcg attggggaac tggacctgct gtttatgtct     420
ctgagaaatg cttgcgtcgg tggaggcggt tcaggcggag gtggctctgg cggtggcgga     480
tcagaggtgc agctgttgga gtctggggga ggcttggtac agcctggggg gtccctgaga     540
ctctcctgtg cagcctctgg attcaccttt agcctgttta cgatgagctg ggtccgccag     600
gctccaggga aggggctgga gtgggtctca gctattagtg gtagtggtgg tagcacatac     660
tacgcagact ccgtgaaggg ccggttcacc atctccagag acaattccaa gaacacgctg     720
tatctgcaaa tgaacagcct gagagccgag gacacggccg tatattactg tgcgaaaagt     780
actcatttgt atcttttttga ctactggggc cagggaaccc tggtcaccgt ctcgagtggc     840
ggtagcggag gggaaattgt gttgacgcag tctccaggca ccctgtcttt gtctccaggg     900
gaaagagcca ccctctcctg cagggccagt cagagtgtta gcatgccgtt tttagcctgg     960
taccagcaga aacctggcca ggctcccagg ctcctcatct atggtgcatc cagcagggcc    1020
actggcatcc agacaggtt cagtggcagt gggtctggga cagacttcac tctcaccatc    1080
agcagactgg agcctgaaga ttttgcagtg tattactgtc agcagatgcg tggtcggccg    1140
ccgacgttcg gccaagggac caaggtggaa atcaaa                              1176

<210> SEQ ID NO 22

<211> LENGTH: 1176
<212> TYPE: DNA
<213> ORGANISM: Artificial Sequence
<220> FEATURE:
<223> OTHER INFORMATION: F8-muIL22 conjugate

<400> SEQUENCE: 22

```
gaggtgcagc tgttggagtc tgggggaggc ttggtacagc ctggggggtc cctgagactc      60
tcctgtgcag cctctggatt cacctttagc ctgtttacga tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaagtact     300
catttgtatc tttttgacta ctggggccag ggaaccctgg tcaccgtctc gagtggcggt     360
agcggagggg aaattgtgtt gacgcagtct ccaggcaccc tgtctttgtc tccaggggaa     420
agagccaccc tctcctgcag ggccagtcag agtgttagca tgccgttttt agcctggtac     480
cagcagaaac ctggccaggc tcccaggctc ctcatctatg gtgcatccag cagggccact     540
ggcatcccag acaggttcag tggcagtggg tctgggacag acttcactct caccatcagc     600
agactggagc ctgaagattt tgcagtgtat tactgtcagc agatgcgtgg tcggccgccg     660
acgttcggcc aagggaccaa ggtggaaatc aaaggtggag gcggttcagg cggaggtggc     720
tctggcggtg gcggatcact gcccgtcaac acccggtgca agcttgaggt gtccaacttc     780
cagcagccgt acatcgtcaa ccgcaccttt atgctggcca aggaggccag ccttgcagat     840
aacaacacag atgtccggct catcggggag aaactgttcc gaggagtcag tgctaaggat     900
cagtgctacc tgatgaagca ggtgctcaac ttcaccctgg aagacgttct gctcccccag     960
tcagacaggt tccagcccta catgcaggag gtggtgcctt cctgaccaa actcagcaat    1020
cagctcagct cctgtcacat cagcggtgac gaccagaaca tccagaagaa tgtcagaagg    1080
ctgaaggaga cagtgaaaaa gcttggagag agtggagaga tcaaggcgat tggggaactg    1140
gacctgctgt ttatgtctct gagaaatgct tgcgtc                              1176
```

<210> SEQ ID NO 23
<211> LENGTH: 392
<212> TYPE: PRT
<213> ORGANISM: Artificial Sequence
<220> FEATURE:
<223> OTHER INFORMATION: muIL22-F8 conjugate

<400> SEQUENCE: 23

```
Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
    50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110
```

```
Arg Arg Leu Lys Glu Thr Val Lys Lys Leu Gly Ser Gly Glu Ile
            115                 120                 125

Lys Ala Ile Gly Glu Leu Asp Leu Leu Phe Met Ser Leu Arg Asn Ala
130                 135                 140

Cys Val Gly Gly Gly Ser Gly Gly Gly Ser Gly Gly Gly
145                 150                 155                 160

Ser Glu Val Gln Leu Leu Glu Ser Gly Gly Gly Leu Val Gln Pro Gly
                165                 170                 175

Gly Ser Leu Arg Leu Ser Cys Ala Ala Ser Gly Phe Thr Phe Ser Leu
            180                 185                 190

Phe Thr Met Ser Trp Val Arg Gln Ala Pro Lys Gly Leu Glu Trp
        195                 200                 205

Val Ser Ala Ile Ser Gly Ser Gly Gly Ser Thr Tyr Tyr Ala Asp Ser
210                 215                 220

Val Lys Gly Arg Phe Thr Ile Ser Arg Asp Asn Ser Lys Asn Thr Leu
225                 230                 235                 240

Tyr Leu Gln Met Asn Ser Leu Arg Ala Glu Asp Thr Ala Val Tyr Tyr
                245                 250                 255

Cys Ala Lys Ser Thr His Leu Tyr Leu Phe Asp Tyr Trp Gly Gln Gly
            260                 265                 270

Thr Leu Val Thr Val Ser Ser Gly Gly Ser Gly Gly Glu Ile Val Leu
        275                 280                 285

Thr Gln Ser Pro Gly Thr Leu Ser Leu Ser Pro Gly Glu Arg Ala Thr
        290                 295                 300

Leu Ser Cys Arg Ala Ser Gln Ser Val Ser Met Pro Phe Leu Ala Trp
305                 310                 315                 320

Tyr Gln Gln Lys Pro Gly Gln Ala Pro Arg Leu Leu Ile Tyr Gly Ala
                325                 330                 335

Ser Ser Arg Ala Thr Gly Ile Pro Asp Arg Phe Ser Gly Ser Gly Ser
            340                 345                 350

Gly Thr Asp Phe Thr Leu Thr Ile Ser Arg Leu Glu Pro Glu Asp Phe
        355                 360                 365

Ala Val Tyr Tyr Cys Gln Gln Met Arg Gly Arg Pro Pro Thr Phe Gly
370                 375                 380

Gln Gly Thr Lys Val Glu Ile Lys
385                 390

<210> SEQ ID NO 24
<211> LENGTH: 392
<212> TYPE: PRT
<213> ORGANISM: Artificial Sequence
<220> FEATURE:
<223> OTHER INFORMATION: F8-muIL22 conjugate

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Phe
            20                  25                  30

Thr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Ser Thr His Leu Tyr Leu Phe Asp Tyr Trp Gly Gln Gly Thr
            100                 105                 110

Leu Val Thr Val Ser Ser Gly Gly Gly Gly Glu Ile Val Leu Thr
        115                 120                 125

Gln Ser Pro Gly Thr Leu Ser Leu Ser Pro Gly Glu Arg Ala Thr Leu
130                 135                 140

Ser Cys Arg Ala Ser Gln Ser Val Ser Met Pro Phe Leu Ala Trp Tyr
145                 150                 155                 160

Gln Gln Lys Pro Gly Gln Ala Pro Arg Leu Leu Ile Tyr Gly Ala Ser
                165                 170                 175

Ser Arg Ala Thr Gly Ile Pro Asp Arg Phe Ser Gly Ser Gly Ser Gly
                180                 185                 190

Thr Asp Phe Thr Leu Thr Ile Ser Arg Leu Glu Pro Glu Asp Phe Ala
                195                 200                 205

Val Tyr Tyr Cys Gln Gln Met Arg Gly Arg Pro Pro Thr Phe Gly Gln
                210                 215                 220

Gly Thr Lys Val Glu Ile Lys Gly Gly Gly Ser Gly Gly Gly Gly
225                 230                 235                 240

Ser Gly Gly Gly Gly Ser Leu Pro Val Asn Thr Arg Cys Lys Leu Glu
                245                 250                 255

Val Ser Asn Phe Gln Gln Pro Tyr Ile Val Asn Arg Thr Phe Met Leu
                260                 265                 270

Ala Lys Glu Ala Ser Leu Ala Asp Asn Asn Thr Asp Val Arg Leu Ile
                275                 280                 285

Gly Glu Lys Leu Phe Arg Gly Val Ser Ala Lys Asp Gln Cys Tyr Leu
                290                 295                 300

Met Lys Gln Val Leu Asn Phe Thr Leu Glu Asp Val Leu Leu Pro Gln
305                 310                 315                 320

Ser Asp Arg Phe Gln Pro Tyr Met Gln Glu Val Val Pro Phe Leu Thr
                325                 330                 335

Lys Leu Ser Asn Gln Leu Ser Ser Cys His Ile Ser Gly Asp Asp Gln
                340                 345                 350

Asn Ile Gln Lys Asn Val Arg Arg Leu Lys Glu Thr Val Lys Lys Leu
                355                 360                 365

Gly Glu Ser Gly Glu Ile Lys Ala Ile Gly Glu Leu Asp Leu Leu Phe
                370                 375                 380

Met Ser Leu Arg Asn Ala Cys Val
385                 390

<210> SEQ ID NO 25
<211> LENGTH: 5
<212> TYPE: PRT
<213> ORGANISM: Artificial Sequence
<220> FEATURE:
<223> OTHER INFORMATION: L19 CDR1 VH

<400> SEQUENCE: 25

Ser Phe Ser Met Ser
1               5

<210> SEQ ID NO 26
<211> LENGTH: 16
<212> TYPE: PRT
<213> ORGANISM: Artificial Sequence
<220> FEATURE:
```

-continued

<223> OTHER INFORMATION: L19 CDR2 VH

<400> SEQUENCE: 26

Ser Ile Ser Gly Ser Ser Gly Thr Thr Tyr Tyr Ala Asp Ser Val Lys
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: L19 CDR3 VH

<400> SEQUENCE: 27

Pro Phe Pro Tyr Phe Asp Tyr
1               5

<210> SEQ ID NO 28
<211> LENGTH: 12
<212> TYPE: PRT
<213> ORGANISM: Artificial Sequence
<220> FEATURE:
<223> OTHER INFORMATION: L19 CDR1 VL

<400> SEQUENCE: 28

Arg Ala Ser Gln Ser Val Ser Ser Ser Phe Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: L19 CDR2 VL

<400> SEQUENCE: 29

Tyr Ala Ser Ser Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: L19 CDR3 VL

<400> SEQUENCE: 30

Gln Gln Thr Gly Arg Ile Pro Pro Thr
1               5

<210> SEQ ID NO 31
<211> LENGTH: 116
<212> TYPE: PRT
<213> ORGANISM: Artificial Sequence
<220> FEATURE:
<223> OTHER INFORMATION: L19 VH domain

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
                100                 105                 110

Thr Val Ser Ser
        115

<210> SEQ ID NO 32
<211> LENGTH: 108
<212> TYPE: PRT
<213> ORGANISM: Artificial Sequence
<220> FEATURE:
<223> OTHER INFORMATION: L19 VL domain

<400> SEQUENCE: 32

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Phe Leu Ala Trp Tyr Gln Gln Lys Pro Gly Gln Ala Pro Arg Leu Leu
             35                  40                  45

Ile Tyr Tyr Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Gly Arg Ile Pro
                 85                  90                  95

Pro Thr Phe Gly Gln Gly Thr Lys Val Glu Ile Lys
                100                 105

<210> SEQ ID NO 33
<211> LENGTH: 229
<212> TYPE: PRT
<213> ORGANISM: Artificial Sequence
<220> FEATURE:
<223> OTHER INFORMATION: L19 diabody

<400> SEQUENCE: 33

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
             35                  40                  45

Ser Ser Ile Ser Gly Ser Ser Gly Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
                100                 105                 110

Thr Val Ser Ser Gly Gly Ser Gly Gly Glu Ile Val Leu Thr Gln Ser
            115                 120                 125
```

```
Pro Gly Thr Leu Ser Leu Ser Pro Gly Glu Arg Ala Thr Leu Ser Cys
    130                 135                 140

Arg Ala Ser Gln Ser Val Ser Ser Phe Leu Ala Trp Tyr Gln Gln
145                 150                 155                 160

Lys Pro Gly Gln Ala Pro Arg Leu Leu Ile Tyr Tyr Ala Ser Ser Arg
                165                 170                 175

Ala Thr Gly Ile Pro Asp Arg Phe Ser Gly Ser Gly Ser Gly Thr Asp
                180                 185                 190

Phe Thr Leu Thr Ile Ser Arg Leu Glu Pro Glu Asp Phe Ala Val Tyr
                195                 200                 205

Tyr Cys Gln Gln Thr Gly Arg Ile Pro Pro Thr Phe Gly Gln Gly Thr
    210                 215                 220

Lys Val Glu Ile Lys
225

<210> SEQ ID NO 34
<211> LENGTH: 5
<212> TYPE: PRT
<213> ORGANISM: Artificial Sequence
<220> FEATURE:
<223> OTHER INFORMATION: F16 CDR1 VH

<400> SEQUENCE: 34

Arg Tyr Gly Met Ser
1               5

<210> SEQ ID NO 35
<211> LENGTH: 17
<212> TYPE: PRT
<213> ORGANISM: Artificial Sequence
<220> FEATURE:
<223> OTHER INFORMATION: F16 CDR2 VH

<400> SEQUENCE: 35

Ala Ile Ser Gly Ser Gly Gly Ser Thr Tyr Tyr Ala Asp Ser Val Lys
1               5                   10                  15

Gly

<210> SEQ ID NO 36
<211> LENGTH: 7
<212> TYPE: PRT
<213> ORGANISM: Artificial Sequence
<220> FEATURE:
<223> OTHER INFORMATION: F16 CDR3 VH

<400> SEQUENCE: 36

Ala His Asn Ala Phe Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: F16 CDR1 VL

<400> SEQUENCE: 37

Gln Gly Asp Ser Leu Arg Ser Tyr Tyr Ala Ser
1               5                   10

<210> SEQ ID NO 38
<211> LENGTH: 7
<212> TYPE: PRT
```

```
<213> ORGANISM: Artificial Sequence
<220> FEATURE:
<223> OTHER INFORMATION: F16 CDR2 VL

<400> SEQUENCE: 38

Gly Lys Asn Asn Arg Pro Ser
1               5

<210> SEQ ID NO 39
<211> LENGTH: 11
<212> TYPE: PRT
<213> ORGANISM: Artificial Sequence
<220> FEATURE:
<223> OTHER INFORMATION: F16 CDR3 VL

<400> SEQUENCE: 39

Asn Ser Ser Val Tyr Thr Met Pro Pro Val Val
1               5                   10

<210> SEQ ID NO 40
<211> LENGTH: 116
<212> TYPE: PRT
<213> ORGANISM: Artificial Sequence
<220> FEATURE:
<223> OTHER INFORMATION: F16 VH domain

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 41
<211> LENGTH: 108
<212> TYPE: PRT
<213> ORGANISM: Artificial Sequence
<220> FEATURE:
<223> OTHER INFORMATION: F16 VL domain

<400> SEQUENCE: 41

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
```

```
                65                  70                  75                  80
Asp Glu Ala Asp Tyr Tyr Cys Asn Ser Ser Val Tyr Thr Met Pro Pro
                        85                  90                  95

Val Val Phe Gly Gly Gly Thr Lys Leu Thr Val Leu
                100                 105

<210> SEQ ID NO 42
<211> LENGTH: 229
<212> TYPE: PRT
<213> ORGANISM: Artificial Sequence
<220> FEATURE:
<223> OTHER INFORMATION: F16 diabody

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
                100                 105                 110

Thr Val Ser Arg Gly Gly Ser Gly Gly Ser Ser Glu Leu Thr Gln Asp
            115                 120                 125

Pro Ala Val Ser Val Ala Leu Gly Gln Thr Val Arg Ile Thr Cys Gln
        130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
                165                 170                 175

Gly Ile Pro Asp Arg Phe Ser Gly Ser Ser Ser Gly Asn Thr Ala Ser
                180                 185                 190

Leu Thr Ile Thr Gly Ala Gln Ala Glu Asp Glu Ala Asp Tyr Tyr Cys
            195                 200                 205

Asn Ser Ser Val Tyr Thr Met Pro Pro Val Val Phe Gly Gly Gly Thr
        210                 215                 220

Lys Leu Thr Val Leu
225

<210> SEQ ID NO 43
<211> LENGTH: 10
<212> TYPE: PRT
<213> ORGANISM: Artificial Sequence
<220> FEATURE:
<223> OTHER INFORMATION: VH and VL domain linker sequence in an scFv
      molecule

<400> SEQUENCE: 43

Gly Gly Gly Ser Gly Gly Gly Ser Gly Gly
1               5                   10
```

The invention claimed is:

1. A conjugate comprising interleukin-22 (IL22) and an antibody molecule, wherein the antibody molecule comprises an antigen-binding site which binds the Extra Domain-A (ED-A) of fibronectin and comprises the complementarity determining regions (CDRs) of antibody F8 set forth in SEQ ID NOs 1-6, and wherein the IL22 comprises the sequence set forth in SEQ ID NO: 11.

2. A conjugate according to claim 1, wherein IL22 is conjugated to the N-terminus of the antibody molecule.

3. A conjugate according to claim 2, wherein IL22 is conjugated to the N-terminus of the antibody molecule via an amino acid linker.

4. The conjugate according to claim 3, wherein the amino acid linker is 10 to 20 amino acids long.

5. The conjugate according to claim 1, wherein the antibody molecule is an antigen-binding fragment.

6. The conjugate according to claim 5, wherein the antigen-binding fragment is a diabody.

7. The conjugate according to claim 5, wherein the antigen-binding fragment comprises a single chain Fv (scFv).

8. The conjugate according to claim 5, wherein the antigen-binding fragment comprises the VH and VL domains of antibody F8 set forth in SEQ ID NOs 7 and 8.

9. The conjugate according to claim 8, wherein the VH domain and the VL domain of the antigen-binding fragment are linked by a 5 to 12 amino acid linker.

10. The conjugate according to claim 9, wherein the antigen-binding fragment comprises the amino acid sequence of F8 set forth in SEQ ID NO: 10.

11. The conjugate according to claim 5, wherein the IL22 is linked to the antigen-binding fragment by an amino acid linker.

12. The conjugate according to claim 5, wherein the antigen-binding fragment comprises a single chain Fv (scFv) and, wherein the IL22 is linked to the N-terminus of the VH domain of the scFv via an amino acid linker.

13. The conjugate according to claim 5, wherein the conjugate comprises the amino acid sequence set forth in SEQ ID NO: 16.

14. A conjugate which binds to the ED-A of fibronectin, wherein the conjugate comprises the amino acid sequence set forth in SEQ ID NO: 16.

15. A conjugate comprising IL22 and an scFv, wherein the scFv comprises an antigen-binding site which binds the ED-A of fibronectin and comprises the CDRs of antibody F8 set forth in SEQ ID NOs 1-6, and wherein the IL22 comprises the sequence set forth in SEQ ID NO: 11 and is linked to the N-terminus of the VH domain of the scFv via an amino acid linker.

* * * * *